United States Patent
Zhang

(10) Patent No.: US 8,611,490 B2
(45) Date of Patent: *Dec. 17, 2013

(54) TETRAHEDRON BEAM COMPUTED TOMOGRAPHY

(75) Inventor: Tiezhi Zhang, Troy, MI (US)

(73) Assignee: William Beaumont Hospital, Royal Oak, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/803,480

(22) Filed: Jun. 29, 2010

(65) Prior Publication Data
US 2011/0002439 A1    Jan. 6, 2011

Related U.S. Application Data

(63) Continuation of application No. 11/786,781, filed on Apr. 12, 2007, now Pat. No. 7,760,849.

(60) Provisional application No. 60/792,207, filed on Apr. 14, 2006.

(51) Int. Cl.
*A61B 6/03* (2006.01)

(52) U.S. Cl.
USPC .......................................................... 378/16

(58) Field of Classification Search
USPC ...................... 378/4, 9, 11, 12, 14, 16, 21, 22
See application file for complete search history.

(56) References Cited

U.S. PATENT DOCUMENTS

| | | | |
|---|---|---|---|
| 3,778,614 A | 12/1973 | Hounsfield | |
| 3,780,291 A | 12/1973 | Stein et al. | |
| 4,132,895 A | 1/1979 | Froggatt | |
| 4,145,613 A | 3/1979 | Bunch | |
| 4,304,999 A | 12/1981 | Richey et al. | |
| 4,315,157 A | 2/1982 | Barnes | |
| 4,380,818 A | 4/1983 | Pfeiler | |
| 4,389,569 A | 6/1983 | Hattori et al. | |
| 4,405,745 A | 9/1983 | Mathis et al. | |
| 4,414,682 A | 11/1983 | Annis et al. | |
| 4,534,051 A | 8/1985 | Grady et al. | |
| 4,547,892 A | 10/1985 | Richey et al. | |

(Continued)

FOREIGN PATENT DOCUMENTS

| | | |
|---|---|---|
| CN | 1419891 A | 5/2003 |
| CN | 1748217 A | 3/2006 |

(Continued)

OTHER PUBLICATIONS

U.S. Appl. No. 11/805,716, filed May 24, 2007, Di Yan et al.

(Continued)

*Primary Examiner* — Glen Kao
(74) *Attorney, Agent, or Firm* — Honigman Miller Schwartz and Cohn LLP; Douglas H. Siegel; Jonathan P. O'Brien

(57) ABSTRACT

A method of imaging an object that includes directing a plurality of x-ray beams in a fan-shaped form towards an object, detecting x-rays that pass through the object due to the directing a plurality of x-ray beams and generating a plurality of imaging data regarding the object from the detected x-rays. The method further includes forming either a three-dimensional cone-beam computed tomography, digital tomosynthesis or Megavoltage image from the plurality of imaging data and displaying the image.

19 Claims, 13 Drawing Sheets

(56) References Cited

U.S. PATENT DOCUMENTS

| | | | |
|---|---|---|---|
| 4,712,226 A | 12/1987 | Horbaschek | |
| 4,920,552 A | 4/1990 | Hermens | |
| 5,039,867 A | 8/1991 | Nishihara et al. | |
| 5,125,012 A | 6/1992 | Schittenhelm | |
| 5,157,707 A | 10/1992 | Ohlson | |
| 5,214,686 A | 5/1993 | Webber | |
| 5,335,255 A | 8/1994 | Seppi et al. | |
| 5,379,333 A | 1/1995 | Toth | |
| 5,394,452 A | 2/1995 | Swerdloff et al. | |
| 5,411,026 A | 5/1995 | Carol | |
| 5,485,494 A | 1/1996 | Williams et al. | |
| 5,521,957 A | 5/1996 | Hansen | |
| 5,533,082 A | 7/1996 | Gronemeyer | |
| 5,602,892 A | 2/1997 | Llacer | |
| 5,625,661 A | 4/1997 | Oikawa | |
| 5,657,364 A | 8/1997 | Pfoh | |
| 5,661,773 A | 8/1997 | Swerdloff et al. | |
| 5,663,995 A | 9/1997 | Hu | |
| 5,675,625 A | 10/1997 | Rockseisen | |
| 5,699,805 A | 12/1997 | Seward et al. | |
| 5,719,914 A | 2/1998 | Rand et al. | |
| 5,724,400 A | 3/1998 | Swerdloff | |
| 5,748,700 A | 5/1998 | Shepherd et al. | |
| 5,751,781 A | 5/1998 | Brown et al. | |
| 5,754,622 A | 5/1998 | Hughes | |
| 5,835,558 A | 11/1998 | Maschke | |
| 5,848,126 A | 12/1998 | Fujita et al. | |
| 5,864,597 A | 1/1999 | Kobayashi | |
| 5,877,501 A | 3/1999 | Ivan et al. | |
| 5,912,943 A | 6/1999 | Deucher et al. | |
| 5,929,449 A | 7/1999 | Huang | |
| 5,949,811 A | 9/1999 | Baba et al. | |
| 5,966,422 A | 10/1999 | Dafni et al. | |
| 5,999,587 A | 12/1999 | Ning et al. | |
| 6,031,888 A | 2/2000 | Ivan et al. | |
| 6,041,097 A | 3/2000 | Roos et al. | |
| 6,113,264 A | 9/2000 | Watanabe | |
| 6,148,058 A | 11/2000 | Dobbs | |
| 6,152,598 A | 11/2000 | Tomisaki et al. | |
| 6,200,024 B1 | 3/2001 | Negrelli | |
| 6,229,870 B1 | 5/2001 | Morgan | |
| 6,256,370 B1 | 7/2001 | Yavuz | |
| 6,259,766 B1 | 7/2001 | Cuppen | |
| 6,269,143 B1 | 7/2001 | Tachibana | |
| 6,285,739 B1 | 9/2001 | Rudin et al. | |
| 6,292,534 B1 | 9/2001 | Linders et al. | |
| 6,307,914 B1 | 10/2001 | Kunieda et al. | |
| 6,318,892 B1 | 11/2001 | Suzuki et al. | |
| 6,325,537 B1 | 12/2001 | Watanabe | |
| 6,345,114 B1 | 2/2002 | Mackie et al. | |
| 6,385,286 B1 | 5/2002 | Fitchard et al. | |
| 6,385,288 B1 | 5/2002 | Kanematsu | |
| 6,389,104 B1 | 5/2002 | Bani-Hashemi et al. | |
| 6,393,096 B1 | 5/2002 | Carol et al. | |
| 6,435,715 B1 | 8/2002 | Betz et al. | |
| 6,463,122 B1 | 10/2002 | Moore | |
| 6,546,073 B1 | 4/2003 | Lee | |
| 6,560,311 B1 | 5/2003 | Shepard et al. | |
| 6,582,121 B2 | 6/2003 | Crain et al. | |
| 6,618,466 B1 | 9/2003 | Ning | |
| 6,628,745 B1 | 9/2003 | Annis et al. | |
| 6,633,627 B2 | 10/2003 | Horiuchi | |
| 6,661,870 B2 | 12/2003 | Kapatoes et al. | |
| 6,707,876 B2 | 3/2004 | Tanigawa | |
| 6,760,402 B2 | 7/2004 | Ghelmansarai | |
| 6,792,074 B2 | 9/2004 | Erbel et al. | |
| 6,842,502 B2 | 1/2005 | Jaffray et al. | |
| 6,865,254 B2 | 3/2005 | Nafstadius | |
| 6,888,919 B2 | 5/2005 | Graf | |
| 6,907,100 B2 | 6/2005 | Taguchi | |
| 6,915,005 B1 | 7/2005 | Ruchala et al. | |
| 6,980,627 B2 | 12/2005 | Qiu et al. | |
| 6,990,175 B2 | 1/2006 | Nakashima et al. | |
| 6,993,112 B2 | 1/2006 | Hesse | |
| 7,030,386 B2 | 4/2006 | Pang et al. | |
| 7,062,006 B1 | 6/2006 | Pelc et al. | |
| 7,072,436 B2 | 7/2006 | Pelc | |
| 7,127,035 B2 | 10/2006 | Anno et al. | |
| 7,145,981 B2 | 12/2006 | Pelc | |
| 7,154,991 B2 | 12/2006 | Earnst et al. | |
| 7,170,975 B2 | 1/2007 | Distler et al. | |
| 7,193,227 B2 | 3/2007 | Hiramoto et al. | |
| 7,227,923 B2 | 6/2007 | Edic et al. | |
| 7,227,925 B1 | 6/2007 | Mansfield et al. | |
| 7,280,631 B2 | 10/2007 | De Man et al. | |
| 7,305,063 B2 | 12/2007 | Heuscher | |
| 7,388,940 B1 | 6/2008 | De Man et al. | |
| 7,428,292 B2 | 9/2008 | De Man et al. | |
| 7,471,765 B2 | 12/2008 | Jaffray et al. | |
| 7,496,181 B2 | 2/2009 | Mazin et al. | |
| 7,657,304 B2 | 2/2010 | Mansfield et al. | |
| 7,760,849 B2* | 7/2010 | Zhang | 378/4 |
| 7,826,592 B2 | 11/2010 | Jaffray et al. | |
| 7,945,021 B2 | 5/2011 | Shapiro et al. | |
| 8,073,104 B2 | 12/2011 | Yan et al. | |
| 2003/0072407 A1 | 4/2003 | Mihara et al. | |
| 2003/0095627 A1 | 5/2003 | Anderton | |
| 2003/0138077 A1 | 7/2003 | Lee | |
| 2003/0191363 A1 | 10/2003 | Boll et al. | |
| 2003/0235271 A1 | 12/2003 | Rand | |
| 2004/0002641 A1 | 1/2004 | Sjogren et al. | |
| 2004/0081270 A1 | 4/2004 | Heuscher | |
| 2004/0086074 A1 | 5/2004 | Taguchi | |
| 2004/0089074 A1 | 5/2004 | Taguch | |
| 2004/0096033 A1 | 5/2004 | Seppi et al. | |
| 2004/0120452 A1 | 6/2004 | Shapiro et al. | |
| 2004/0174949 A1 | 9/2004 | Yamashita et al. | |
| 2004/0254448 A1 | 12/2004 | Amies et al. | |
| 2005/0013404 A1 | 1/2005 | Kasperl et al. | |
| 2005/0027196 A1 | 2/2005 | Fitzgerald | |
| 2005/0054937 A1 | 3/2005 | Takaoka et al. | |
| 2005/0058237 A1 | 3/2005 | Morf | |
| 2005/0080336 A1 | 4/2005 | Byrd et al. | |
| 2005/0085710 A1 | 4/2005 | Earnst et al. | |
| 2005/0111610 A1 | 5/2005 | De Man et al. | |
| 2005/0111616 A1 | 5/2005 | Li et al. | |
| 2005/0111621 A1 | 5/2005 | Riker et al. | |
| 2005/0197564 A1 | 9/2005 | Dempsey | |
| 2005/0234327 A1 | 10/2005 | Saracen et al. | |
| 2005/0249432 A1 | 11/2005 | Zou et al. | |
| 2005/0251029 A1 | 11/2005 | Khamene et al. | |
| 2006/0002506 A1 | 1/2006 | Pelc | |
| 2006/0008047 A1 | 1/2006 | Zhou et al. | |
| 2006/0017009 A1 | 1/2006 | Rink et al. | |
| 2006/0239409 A1 | 10/2006 | Levene et al. | |
| 2006/0245543 A1 | 11/2006 | Earnst et al. | |
| 2006/0259282 A1 | 11/2006 | Failla et al. | |
| 2006/0269049 A1 | 11/2006 | Yin et al. | |
| 2006/0274885 A1 | 12/2006 | Wang et al. | |
| 2006/0285639 A1 | 12/2006 | Olivera et al. | |
| 2006/0285640 A1 | 12/2006 | Nizin et al. | |
| 2006/0285641 A1 | 12/2006 | Scherch | |
| 2007/0003123 A1 | 1/2007 | Fu et al. | |
| 2007/0016014 A1 | 1/2007 | Hara et al. | |
| 2007/0019782 A1 | 1/2007 | Van Stevendaal et al. | |
| 2007/0053492 A1 | 3/2007 | Kidani et al. | |
| 2007/0076846 A1 | 4/2007 | Ruchala et al. | |
| 2007/0280408 A1 | 12/2007 | Zhang | |
| 2010/0119032 A1 | 5/2010 | Yan et al. | |
| 2010/0135454 A1 | 6/2010 | Noo | |
| 2011/0002439 A1 | 1/2011 | Zhang | |
| 2011/0080992 A1 | 4/2011 | Dafni | |
| 2011/0211666 A1 | 9/2011 | Ying et al. | |

FOREIGN PATENT DOCUMENTS

| | | |
|---|---|---|
| CN | 1758876 A | 4/2006 |
| DE | 1992708 U | 8/1968 |
| DE | 28 22 241 A1 | 12/1978 |
| EP | 0314231 A2 | 5/1989 |
| EP | 0922943 A2 | 6/1999 |
| JP | 52-52594 A | 4/1977 |
| JP | 56-101579 A | 8/1981 |
| JP | 56-168578 A | 12/1981 |

(56) References Cited

FOREIGN PATENT DOCUMENTS

| | | |
|---|---|---|
| JP | 5894835 A | 6/1983 |
| JP | 4242736 A | 8/1992 |
| JP | 4-307035 | 10/1992 |
| JP | 5-172764 A | 7/1993 |
| JP | 07255717 A | 10/1995 |
| JP | 10113400 A | 5/1998 |
| JP | 10511595 A | 11/1998 |
| JP | 10328318 A | 12/1998 |
| JP | 11-047290 | 2/1999 |
| JP | 11099148 A | 4/1999 |
| JP | 11160440 A | 6/1999 |
| JP | 2000308634 A | 11/2000 |
| JP | 2000308634 A | 11/2000 |
| WO | 9713552 A1 | 4/1997 |
| WO | 9852635 A1 | 11/1998 |
| WO | 9903397 A1 | 1/1999 |
| WO | WO2004061744 A2 | 7/2004 |
| WO | WO2004080309 A2 | 9/2004 |
| WO | WO2006018761 A1 | 2/2006 |

OTHER PUBLICATIONS

Zhang, J., et al., "A Multi-Beam X-Ray Imaging System Based on Carbon Nanotube Field Emitters," Medical Imaging 2006: Physics of Medical Imaging Proceedings of SPIE, vol. 6142, (2006), eight pages.

Schmidt, T.G., et al., "A Prototype Table-Top Inverse-Geometry Volumetric CT Images," Med. Phys. vol. 33, No. 6 (Jun. 2006) pp. 1867-1878.

Shihaliev, P.M., et al., "Photon Counting Computed Tomography: Concept and Initial Results," Med. Phys., vol. 32, No. 2, (Feb. 2005), abstract.

Webb, S., et al., Abstract of "Monte Carlo Modelling of the Performance of a Rotating Slit-collimator for Improved Planar Gamma-Camera Imaging," Phys. Med. Biol., vol. 37, No. 5, (May 1992), abstract.

Gupta, N.K., et al., "Tangential CT, A Computed Tomography Method Developed for Industrial Inspection," 16th WCNDT 2004, (Sep. 2004), five pages.

Zeng. G.L., et al., "Image Reconstruction Algorithm for a SPECT System with a Convergent Rotating Slat Collimator," IEEE Transactions on Nuclear Science, vol. 51, No. 1, (Feb. 2004), pp. 142-148.

EP Search Report dated Apr. 15, 2011 for corresponding European Patent Application No. 07 75 5309.

Zhang, Tiezhi, et al., "Tetrahedron beam computed tomography (TBCT): a new design of volumetric CT system," Phys. Med. Biol., vol. 54, 2009, pp. 3365-3378.

Xu, Xiaochao, et al., "A tetrahedron beam computed tomography benchtop system with a multiple pixel field emission x-ray tube," Med. Phys., vol. 3, No. 10, Oct. 2011, pp. 5500-5508.

Antonuk, L.E., et al., "A Real-Time, Flat-Panel, Amorphous Silicon, Digital X-Ray Imager", Radiographics, vol. 15, No. 4, Jul. 1995, pp. 993-1000.

Antonuk, L.E., et al., "Initial Performance Evaluation of an Indirect-Detection, Active Matrix Flat-Panel Imager (AMFPI) Prototype for Megavoltage Imaging", Int. J. Radiat. Oncol. Biol. Phys., vol. 42, No. 2, 1998, pp. 437-454.

Antonuk, L.E., et al., "Megavoltage Imaging with a Large-Area, Flat-Panel, Amorphous Silicon Imager", Int. J. Radiat. Oncol. Biol. Phys., vol. 36, No. 3, 1996, pp. 661-672.

Antonuk, L.E., et al., "Strategies to Improve the Signal and Noise Performance of Active Matrix, Flat-Panel Imagers for Diagnostic X-Ray Applications", Med. Phys., vol. 27, No. 2, Feb. 2000, pp. 289-306.

Basset, P.G., Wong, J.W. and Aspin, N.: "An Interactive Computer System for Studying Human Mucociliary Clearance", Computer Biol. Med. 1979, vol. 9, pp. 97-105.

Birkner, M., et al., "Adapting Inverse Planning to Patient and Organ Geometrical Variation: Algorithm and Implementation," Med. Phys., vol. 30, No. 10, Oct. 2003, pp. 2822-2831.

Bissonnette, J.P., et al., "Optimal Radiographic Magnification for Portal Imaging.", Med. Phys., vol. 21, No. 9, Sep. 1994, pp. 1435-1445.

Boyer, A.L., et al., (IMRT Collaborative Working Group): "Intensity-modulated radiotherapy: Current status and issues of interest", Int. J. Radiat. Oncol. Biol. Phys. 2001, vol. 51, No. 4, pp. 880-914.

Boyer, A.L., et al., "A Review of Electronic Portal Imaging Devices (EPIDs)", Medical Physics, Jan./Feb. 1992, vol. 19, No. 1, pp. 19: 1-16.

Brown, A.P., et al., "Three-Dimensional Photon Treatment Planning for Hodgkin's Disease", Int. J. Radiat. Oncol. Biol. Phys., May 15, 1991, vol. 21, No. 1, pp. 205-215.

Chen, J., et al., "Dose-Guided Radiation Therapy with Megavoltage Cone-Beam CT," published by the British Journal of Radiology, vol. 79, 2006, pp. S87-S98.

Cheng, A., et al., "Systematic Verification of a Three-Dimensional Electron Beam Dose Calculation Algorithm", Med. Phys., 1996, vol. 23, No. 5, pp. 685-693.

Chi, Y., et al., "A Material Sensitivity Study on the Accuracy of Deformable Organ Registration Using Linear Biomechanical Models," Med. Phys., vol. 33: No. 2, Feb. 2006, pp. 421-433.

Cullity, B.D., "Elements of X-Ray Diffraction, Second Edition," (Reading, MA: Addison Wesley, 1978), p. 6-12.

Dieu, L., et al., "Ion Beam Sputter-Deposited SiN/TiN Attenuating Phase-Shift Photoblanks," publication source and date unknown, 8 pages.

Drake, D.G., et al., "Characterization of Fluoroscopic Imaging System for kV and MV Radiography", Med. Phys., May 2000, vol. 27, No. 5, pp. 898-905.

Du, M.N., et al., "A Multileaf Collimator Field Prescription Preparation System for Conventional Radiotherapy", Int. J. Radiat. Oncol. Biol. Phys., 1994, vol. 30, No. 3, pp. 707-714.

Du, M.N., et al., "A Multileaf Collimator Field Prescription Preparation System for Conventional Radiotherapy", Int. J. Radiat. Oncol. Biol. Phys., 1995, vol. 32, No. 2, pp. 513-520.

El-Mohri, Y., et al., "Relative Dosimetry Using Active Matrix Flat-Panel Imager (AMFPI) Technology", Med. Phys., Aug. 1999, vol. 26, No. 8, pp. 1530-1541.

Ezz, A., et al., "Daily Monitoring and Correction of Radiation Field Placement Using a Video-Based Portal Imaging System: a Pilot Study", Int. J. Radiat. Oncol. Biol. Phys., 1992, vol. 22, No. 1, pp. 159-165.

Frazier, A., et al., "Dosimetric Evaluation of the Conformation of the Multileaf Collimator to Irregularly Shaped Fields", Int. J. Radiat. Oncol.Biol. Phys., 1995, vol. 33, No. 5, pp. 1229-1238.

Frazier, A., et al., "Effects of Treatment Setup Variation on Beam's Eye View Dosimetry for Radiation Therapy Using the Multileaf Collimator vs. The Cerrobend Block", Int. J. Radiat. Oncol. Biol. Phys., 1995, vol. 33, No. 5, pp. 1247-1256.

Ghilezan, M., et al., "Online Image-Guided Intensity-Modulated Radiotherapy for Prostate Cancer: How Much Improvement Can We Expect? A Theoretical Assessment of Clinical Benefits and Potential Dose Escalation by Improving Precision and Accuracy of Radiation Delivery," Int. J. Radiation Oncology Biol. Phys., vol. 60, No. 5, 2004, pp. 1602-1610.

Graham, M.L., et al., "A Method to Analyze 2-Dimensional Daily Radiotherapy Portal Images from an On-Line Fiber-Optic Imaging System.", Int. J. Radiat. Oncol. Biol. Phys., Mar. 1991, vol. 20, No. 3, pp. 613-619.

Halverson, K.J., et al., "Study of Treatment Variation in the Radiotherapy of Head and Neck Tumors Using a Fiber-Optic On-Line Line Radiotherapy Imaging System", Int. J. Radiat. Oncol. Biol. Phys., Oct. 1991, vol. 21, No. 5, pp. 1327-1336.

Harms, W.B., Sr., et al., "A Software Tool for the Quantitative Evaluation of 3D Dose Calculation Algorithms", Med. Phys., Oct. 1998, vol. 25, No. 10, pp. 1830-1839.

Herman, M.G., et al. "Clinical use of electronic portal imaging: Report of AAPM Radiation Therapy Committee Task Group 58", Med. Phys. May 2001, vol. 28, No. 5, pp. 712-737.

International Search Report for PCT/US2007/008996, dated Mar. 4, 2008, three pages.

(56) References Cited

OTHER PUBLICATIONS

Jaffray, et al., Cone-Beam CT: Applications in Image-Guided External Beam Radiotherapy and Brachytherapy, publication source unknown, date unknown, one page.
Jaffray, et al., "Conebeam Tomographic Guidance of Radiation Field Placement for Radiotherapy of the Prostate," Manuscript accepted for publication in the International Journal of Radiation Oncology, Biology, Oct. 1998, 32 pages.
Jaffray, et al., "Exploring 'Target of the Day' Strategies for a Medical Linear Accelerator with Conebeam-CT Scanning Capability," XIIth ICCR held in Salt Lake City, Utah, May 27-30, 1997, pp. 172-174.
Jaffray, et al., "Flat-Panel Cone-Beam CT for Image-Guided External Beam Radiotherapy," publication source unknown, Oct. 1999, 36 pages.
Jaffray, et al., "Managing Geometric Uncertainty in Conformal Intensity-Modulated Radiation Therapy," Seminars in Radiation Oncology, vol. 9, No. 1, Jan. 1999 pp. 4-19.
Jaffray, et al., "Performance of a Volumetric CT Scanner Based Upon a Flat-Panel Imager," SPIE Physics of Medical Imaging, vol. 3659, Feb. 1999, pp. 204-214.
Jaffray, D.A., et al., "A Radiographic and Tomographic Imaging System Integrated into a Medical Linear Accelerator for Localization of Bone and Soft-Tissue Targets", Int. J. Radiat. Oncol. Biol. Phys., 1999, vol. 45, No. 3, pp. 773-789.
Jaffray, D.A., et al., "Activity Distribution of a Cobalt-60 Teletherapy Source", Med. Phys., Mar./Apr. 1991, vol. 18, No. 2, pp. 288-291.
Jaffray, D.A., et al., "Cone-Beam Computed Tomography with a Flat-Panel Imager: Initial Performance Characterization", Med. Phys. Jun. 2000, vol. 27, No. 6, pp. 1311-1323.
Jaffray, et al., "Cone-Beam Computed Tomography with a Flat-Panel Imager: Initial Performance Characterization," Submission to the Medical Physics Journal for publication on Aug. 1999, 36 pages.
Jaffray, D.A., et al., "Dual-Beam Imaging for Online Verification of Radiotherapy Field Placement", Int. J. Radiat. Oncol. Biol. Phys., 1995, vol. 33, No. 5, pp. 1273-1280.
Jaffray, D.A., et al., "X-Ray Scatter in Megavoltage Transmission Radiography: Physical Characteristics and Influence on Image Quality", Med. Phys., Jan. 1994, vol. 21, No. 1, pp. 45-60.
Jaffray, D.A., et al., "X-Ray Sources of Medical Linear Accelerators: Focal and Extra-Focal Radiation", Med. Phys. Sep./Oct. 1993, vol. 20, No. 5, pp. 1417-1427.
Kapatoes, J.M., et al., "On the Accuracy and Effectiveness of Dose Reconstruction for Tomotherapy," Phys. Med. Biol., vol. 46, 2001, pp. 943-966.
Kessler, M.L., "Image Registration and Data Fusion in Radiation Therapy," The British Journal of Radiology, vol. 79, 2006, pp. S99-S108.
Kestin, L.L., et al., "Improving the Dosimetric Coverage of Interstitial High-Dose-Rate Breast Implants", Int. J. Radiat. Oncol. Biol. Phys., 2000, vol. 46, No. 1, pp. 35-43.
Kestin, L.L., et al., "Intensity Modulation to Improve Dose Uniformity with Tangential Breast Radiotherapy: Initial Clinical Experience" Int J. Radiat. Oncol. Biol. Phys., 2000, vol. 48, No. 5, pp. 1559-1568.
Kini, V.R., et al., "Use of Three-Dimensional Radiation Therapy Planning Tools and Intraoperative Ultrasound to Evaluate High Dose Rate Prostate Brachytherapy Implants", Int. J. Radiat. Oncol. Biol. Phys., 1999, vol. 43, No. 3, pp. 571-578.
Kress, J., et al. "Patient position verification using CT images" Medical Physics, AIP, 26(6) 1999, 941-948.
Laughlin, J.S., et al., (writing chairs), "Evaluation of High Energy Photon External Beam Treatment Planning: Project Summary", Int. J. Rad. Oncol. Biol. Physics. 1991, vol. 21, pp. 3-8.
Liang, J., et al., "Reducing Uncertainties in Volumetric Image Based Deformable Organ Registration," Med. Phys., vol. 30, No. 8, Aug., 2003, pp. 2116-2122.
Lockman, D., et al., "Estimating the Dose Variation in a Volume of Interest with Explicit Consideration of Patient Geometric Variation," Med. Phys., vol. 27, No. 9, Sep. 2000, pp. 2100-2108.

Martinez, A., et al., "Improvement in dose escalation using the process of adaptive radiation therapy combined with three dimensional conformal or Intensity modulated beams for prostate cancer", Int. J. Radiat. Oncol. Biol. Phys. 2001, vol. 50, No. 5, pp. 1226-1234.
Masterson, M.E., et al., "Inter-Institutional Experience in Verification of External Photon Dose Calculations", Int. J. Rad. Oncol. Biol. Physics, 1991, vol. 21, pp. 37-58.
Michalski, J., et al., "An Evaluation of Two Methods of Anatomical Alignment of Radiotherapy Portal Images", Int. J. Radiat. Oncol. Biol. Phys., 1993; vol. 27. No. 5, pp. 1199-1206.
Michalski, J.M., et al., "Prospective Clinical Evaluation of an Electronic Portal Imaging Device", Int. J. Radiat. Oncol. Biol. Phys., 1996, vol. 34, No. 4, pp. 943-951.
Michalski, J.M., et al., "The Use of On-Line Image Verification to Estimate the Variation in Radiation Therapy Dose Delivery", Int. J. Radiat. Oncol. Biol. Phys., 1993, vol. 27, No. 3, pp. 707-716.
Milliken, B.D., et al., "Verification of the Omni Wedge Technique", Med. Phys. Aug. 1998, vol. 25, No. 8, pp. 1419-1423.
Mohan, R. (writing chair), "Three-Dimensional Dose Calculations for Radiation Treatment Planning", Int. J. Rad. Oncol. Biol. Physics, May 15, 1991; vol. 21, No. 1, pp. 25-36.
Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)," publication source unknown, (publication date unknown), 4 pages, while the date of publication is unknown, it is believe that the article was publicly available before May 24, 2007.
Oldham, M., et al., "Practical aspects of in situ 160(y,n)150 activation using a conventional medical accelerator for the purpose of perfusion imaging", Med. Phys. Aug. 2001; vol. 28, No. 8, pp. 1669-1678.
Perera, H., et al., "Rapid Two-Dimensional Dose measurement in Brachytherapy Using Plastic Scintillator Sheet: Linearity, Signal-to-Noise Ratio, and Energy Response Characteristics.", Int. J. Radiat. Oncol. Biol. Phys., 1992, vol. 23, No. 5, pp. 1059-1069.
Pisani, L., et al., "Setup Error in Radiotherapy: On-line Correction Using Electronic Kilovoltage and Megavoltage Radiographs", Int. J. Radiat. Oncol. Biol. Phys., 2000, vol. 47, No. 3, pp. 825-839.
Purdy, J.A., et al., "State of the Art High Energy Photon Treatment Planning", Front Radiat. Ther. Oncol., 1987, vol. 21, pp. 4-24.
Schaly, B., et al., "Tracking the Dose Distribution in Radiation Therapy by Accounting for Variable Anatomy," Phys. Med. Biol., vol. 49, 2004, pp. 791-805.
Sharpe, M.B., et al., "Compensation of X-Ray Beam Penumbra in Conformal Radiotherapy", Med. Phys., Aug. 2000, vol. 27, No. 8, pp. 1739-1745.
Sharpe, M.B., et al., "Monitor Unit Settings for Intensity Modulated Beams Delivered Using a Step-and-Shoot Approach", Med. Phys., Dec. 2000, vol. 27, No. 12, pp. 2719-2725.
Shiu, A.S., et al., "Verification Data for Electron Beam Dose Algorithms", Med. Phys., May/Jun. 1992, vol. 19, No. 3, pp. 623-636.
Siewerdsen, et al., "Cone-Beam CT with a Flat-Panel Imager: Noise Consideration for Fully 3-D Computed Tomography," SPIE Physics of Medical Imaging, vol. 3336, Feb. 2000, pp. 546-554.
Siewerdsen, et al., "Optimization of X-Ray Imaging Geometry (with SpecificApplication to Flat-Panel Cone-Beam Computed Tomography)," Non-Final Version of Manuscript to be published in Med. Phys., vol. 27, No. 8, Aug. 2000, pp. 1-12.
Siewerdsen, J.H., et al., "A Ghost Story: Spatio-Temporal Response Characteristics of an Indirect-Detection Flat-Panel Imager", Med. Phys., Aug. 1999, vol. 26, No. 8, pp. 1624-1641.
Siewerdsen, et al., "Cone-Beam Computed Tomography with a Flat-Panel Imager: Effects of Image Lag," Med. Phys., vol. 26, No. 12, Dec. 1999, pp. 2635-2647.
Siewerdsen, J.H., et al., "Cone-Beam Computed Tomography with a Flat-Panel Imager: Magnitude and Effects of X-Ray Scatter", Med. Phys., Feb. 2001, vol. 28, No. 2, pp. 220-231.
Siewerdsen, J.H., et al., "Empirical and Theoretical Investigation of the Noise Performance of Indirect Detection, Active Matrix Flat-Panel Imagers (AMFPIs) for Diagnostic Radiology", Med. Phys., Jan. 1997, vol. 24, No. 1, pp. 71-89.

(56) References Cited

OTHER PUBLICATIONS

Siewerdsen, J.H., et al., "Optimization of X-Ray Imaging Geometry (with Specific Application to Flat-Panel Cone-Beam Computed Tomography)", Med. Phys., Aug. 2000, vol. 27, No. 8, pp. 1903-1914.
Siewerdsen, JH, et al., "Signal, Noise Power Spectrum, and Detective Quantum Efficiency of Indirect-Detection Flat-Panel Panel Imagers for Diagnostic Radiology", Med. Phys., May 1998, vol. 25, No. 5, pp. 614-628.
Sohn, M. et al., "Modeling Individual Geometric Variation Based on Dominant Eigenmodes of Organ Deformation: Implementation and Evaluation," Phys Med Biol, vol. 50, 2005, pp. 5893-908.
Sontag, M.R. And Purdy, J.A. (writing chairs), "State of the Art of External Photon Beam Radiation Treatment Planning", Int. J. Rad. Oncol. Biol. Physics. 1991, vol. 21 No. 1, pp. 9-23.
Stromberg, J.S., et al., "Active Breathing Control (ABC) for Hodgkin's Disease: Reduction in Normal Tissue Irradiation with Deep Inspiration and Implications for Treatment", Int. J. Radiat. Oncol. Biol. Phys. 2000, vol. 48, No. 3, pp. 797-806.
Teicher, B.A., et al., "Allosteric Effectors of Hemoglobin as Modulators of Chemotherapy and Radiation Therapy in Vitro and in Vivo", Cancer Chemother. Pharmacol., 1998, vol. 42, pp. 24-30.
Tepper, J.E. and Shank, B. (writing Chairs), "Three-Dimensional Display in Planning Radiation Therapy: A Clinical Perspective", Int. J. Rad. Oncol. Biol. Physics. 1991, vol. 21, No. 1, pp. 79-89.
Urie, M.M., et al., "The Role of Uncertainty Analysis in Treatment Planning", Int. J. Radiat. Oncol. Biol. Phys., 1991, vol. 21, No. 1, pp. 91-107.
Vicini, F.A., et al., "Low-Dose-Rate Brachytherapy as the Sole Radiation Modality in the Management of Patients with Early-Stage Breast Cancer Treated with Breast-Concerving Therapy: Preliminary Results of a Pilot Trial", Int. J. Radiat. Oncol. Biol. Phys., 1997, vol. 38, No. 2, pp. 301-310.
Vicini, F.A., et al., "Dose-Volume Analysis for Quality Assurance of Interstitial Brachytherapy for Breast Cancer", Int. J. Radiat. Oncol. Biol. Phys., 1999, vol. 45, No. 3, pp. 803-810.
Vicini, F.A., et al., "Implementation of a 3D-Virtual Brachytherapy in the Management of Breast Cancer: a Description of a New Method of Interstitital Brachytherapy", Int. J. Radiat. Oncol. Biol. Phys., 1998, vol. 40, No. 3, pp. 629-635.
Weinberg, R., et al., "Dosimetric Uncertainties of Three-Dimensional Dose Reconstruction from Two-Dimensional Data in a Multi-Institutional Study," Journal of Applied Clinical Medical Physics, vol. 5, No. 4, Fall 2004, pp. 15-28.
Vvilliamson, J.F., et al., "One-Dimensional Scatter-Subtraction Method for Brachytherapy Calculation Near Bounded Heterogeneities", Med. Phys., Jan./Feb. 1993, vol. 20, No. 1, pp. 233-244.
Wong, J.K., et al., "Conservative Management of Osteoradionecrosis", Oral Surg. Oral Med. Pahol. Oral Pathol., Jul. 1997, vol. 84, No. 1, pp. 16-21.
Wong, J.W., et al., "Development of a Second-Generation Fiber-Optic On-Line Image Verification System", Int. J. Radiat. Oncol. Biol. Phys., 1993, vol. 26, No. 2, pp. 311-320.
Wong, J.W., et al., "Effect of Small Inhomogeneities on Dose in a Cobalt-60 Beam", Med. Phys., Nov./Dec. 1981, vol. 8, No. 6, pp. 783-791.
Wong, J.W., et al., "On Methods of Inhomogeneity Corrections for Photon Transport", Med. Phys., Sep./Oct. 1990, vol. 17, No. 5, pp. 807-814.
Wong, J.W., et al., "On-Line Image Verification in Radiation Therapy: An Early USA Experience", Med. Prog. Through Technol., 1993, vol. 19, pp. 43-54.
Wong, J.W., et al., "On-Line Radiotherapy Imaging with an Array of Fiber-Optic Image Reducers", Int. J. Radiat. Oncol. Biol. Phys., Jun. 1990, vol. 18, No. 6, pp. 1477-1484.
Wong, J.W., et al., "Portal Dose Images. I: Quantitative Treatment Plan Verification", Int. J. Radiat. Oncol.Biol.Phys., Jun. 1990, vol. 18, No. 6, pp. 1455-1463.

Wong, J.W., et al., "Reconsideration of the Power-Law (Batho) Equation for Inhomogeneity Corrections", Med. Phys., Jul./Aug. 1982, vol. 9, No. 4, pp. 521-530.
Wong, J.W., et al., "Second Scatter Contribution to Dose in Cobalt-60 Beam" Med. Phys., Nov./Dec. 1981, vol. 8, No. 6, pp. 775-782.
Wong, J.W., et al., "The Cumulative Verification Image Analysis Tool for Offline Evaluation of Portal Images", Int. J. Radiat. Oncol.Biol. Phys., 1995, vol. 33, No. 5, pp. 1301-1310.
Wong, J.W., et al., "The Use of Active Breathing Control (ABC) to Reduce Margin for Breathing Motion", Int. J. Radiat. Oncol. Biol. Phys., 1999, vol. 44, No. 4, pp. 911-919.
Wong, J.W., et al., "Treatment Verifications and Patient Dose Estimations Using Portal Dose Imaging" Radiotherapy System Research (Japan). 1988; vol. 5, No. 3, pp. 213-225.
Wong, J.W., et al.; "A New Approach to CT Pixel-Based Photon Dose Calculations in Heterogeneous Media", Med. Phys., Mar./Apr. 1983, vol. 10, No. 2, pp. 199-208.
Wong, J.W., (writing chair), "Role of Inhomogeneity Corrections in 3D Photon Treatment Planning", Int. J. Rad. Oncol. Biol. Physics. 1991, vol. 21, No. 1, pp. 59-69.
Wu, Y., et al., "Implementing multiple static field delivery for intensity modulated beams", Med. Phys., Nov. 2001, vol. 28, No. 11, pp. 2188-2197.
Yan, D., et al., "The influence of interpatient and intrapatient rectum variation on external beam treatment of prostate cancer", Int. J. Radiat. Oncol. Biol. Phys. 2001, vol. 51, No. 4, pp. 1111-1119.
Yan, D., et al., "Organ/Patient Geometric Variation in External Beam Radiotherapy and Its Effect," Med. Phys., vol. 28, No. 4, Apr. 2001, pp. 593-602.
Yan, D., "Adapt Radiotherapy to Temporal Biological Targets Assessed Using Biological Images," publication source unknown, while the date of publication is unknown, it is believe that the article was publicly available before May 24, 2007, 3 pages.
Yan, D., "Image-Guided Adaptive Radiotherapy Model," AAPM, Mar. 10, 2006, pp. 1-15.
Yan, D., "Image-Guided/Adaptive Radiotherapy," Medical Radiology-Radiation Oncology, Volume: New Technologies in Radiation Oncology, Edited by W. Schlegel, T. Bortfeld and Al Grosu, Springer-Verlag, Berlin, Heidelberg, New York, Hong Kong, Sep. 8, 2005, ISBN 3-540-00321-5, pp. 317-332.
Yan, D., "Treatment Strategy for Daily Image Feedback Adaptive Radiotherapy," Proceeding, XIIIth International Conference on The Use of Computers in Radiotherapy, Heidelberg, Germany, 2000, pp. 518-520.
Yan, D., et al., "A Model to Accumulate Fractionated Dose in a Deforming Organ," Int. J. Radiation Oncology Biol. Phys., vol. 44, No. 3, 1999, pp. 665-675.
Yan, D., et al., "Adaptive Modification of Treatment Planning to Minimize the Deleterious Effects of Treatment Setup Errors," Int. J. Radiation Oncology Biol. Phys., vol. 37, No. 5, while the publication date is unknown, it is believed to have been published prior to 1999, pp. 1-27.
Yan, D., et al., "Adaptive Radiation Therapy," Phys. Med. Biol., vol. 42, 1997, pp. 123-132.
Yan, D., et al., "An Off-Line Strategy for Constructing a Patient-Specific Planning Target Volume For Image Guided Adaptive Radiotherapy of Prostate Cancer," Int. J. Radiation Oncology Biol. Phys., vol. 48, No. 1, 2000, pp. 289-302.
Yan, D., et al., "The Use of Adaptive Radiation Therapy to Reduce Setup Error: A Prospective Clinical Study," Int. J. Radiation Oncology Biol. Phys., vol. 41, No. 3, 1998, pp. 715-720.
Yan, D., et al., "Strategies for Off-Line and On-Line Image Feedback Adaptive Radiotherapy," Editors: BK Paliwal, DE Herbert, JF Fowler, MP Mehta, Biological & Physical Basis of IMRT & Tomotherapy, AAPM Symposium Proceeding No. 12, 2002, pp. 139-150.
Yan, D., et al., "Computed Tomography Guided Management of Interfractional Patient Variation," Semin. Radiat. Oncol. vol. 15, 2005, pp. 168-179.
Yan, D., et al., "A New Model for "Accept or Reject" Strategies in Off-Line and On-Line Megavoltage Treatment Evaluation", Int. J. Radiat. Oncol. Biol. Phys., 1995, vol. 31, No. 4, pp. 943-952.

(56) References Cited

OTHER PUBLICATIONS

Yan, D., et al., "Adaptive Modification of Treatment Planning to Minimize the Deleterious effects of Treatment Setup Errors", Int. J. Radiat. Oncol. Biol. Phys., 1997, vol. 38, No. 1, pp. 197-206.
Yang, Y., et al., "Evaluation of On-Board kV Cone Beam CT (CBCT)-based Dose Calculation," Phys. Med. Biol., vol. 52, 2007, pp. 685-705.
Ying, X.G., et al., "Portal Dose Images. II: Patient Dose Estimation", Int. J. Radiat. Oncol. Biol. Phys., Jun. 1990, vol. 18, No. 6, pp. 1465-1475.
Yu, C.X., et al., "Photon Dose Calculation Incorporating Explicit Electron Transport", Med. Phys., Jul. 1995, vol. 22, No. 7, pp. 1157-1165.
Yu, C.X., et al., "A Method for Implementing Dynamic Photon Beam Intensity Modulation Using Independent Jaws and a Multileaf Collimator", Phys. Med. Biol., 1995, vol. 40, pp. 769-787.
Yu, C.X., et al., "A Multiray Model for Calculating Electron Pencil Beam Distribution", Med. Phys., Sep./Oct. 1988, vol. 15, No. 5, pp. 662-671.
Yu, C.X., et al., "Photon Dose Perturbations Due to Small Inhomogeneities", Med. Phys., Jan./Feb. 1987, vol. 14, No. 1, pp. 78-83.
Zhang, T., et al., "Automatic Delineation of Online Head and Neck CT Images: Towards Online Adaptive Radiotherapy," Int. J. of Radiation Oncology Biol. Phys., vol. 68, No. 2, 2007, pp. 522-530.
Lucas, "Analysis of surface dose variation in CT procedures." The British Journal of Radiology, 74 (2001), 1128-1136.
Kim, L., et al., "Volumetric Modulated Arc Therapy Using a Rotating Couch: An Accelerated Partial Breast Irradiation Planning Study," Int. L. Radiation Oncology Biol. Phys., vol. 75, Issue 3, Supplement 1, Nov. 1, 2009, pp. S732-S733.
Nakagawa, K. et al., "development of a megavoltage ct scanner using linear accelerator treatment beam", Journal of Jastro, vol. 3, No. 4, pp. 265-276, 1991, Japanese Society for Therapeutic Radiology and Oncology.
Shirato, H., "real-time tumor tracking radiotherapy and stereotactic irradiation", Monthly New Medical Care, vol. 26, No. 12, pp. 61-63, 1999, ME Co., Ltd.
Vicini F et al. "NSABP/RTOG 0413: A randomized phase III study of conventional whole breast irradiation versus partial breast irradiation for women with Stage 0, I, or II breast cancer", 2007.
Hepel, Jaroslaw T. et al. "Toxicity of three-dimensional conformal radiotherapy for accelerated partial breast irradiation" Int. J. Radiat. Oncol. Biol. Phys., vol. 75, No. 5, 2009, pp. 1290-1296.
Jagsi Reshma et al. "Unacceptable cosmesis in a protocol investigating intensity modulated radiotherapy with active breathing control for accelerated partial breast irradiation" Int. J. Radiat. Oncol. Biol. Phys. Vo. 76, No. 1, 2009, pp. 71-78.
Livi, Lorenzo et al. "Accelerated partial breast irradiation with IMRT: new technical approach and interim analysis of acute toxicity in a phase III randomized clinical trial" Int. J. Radiat. Oncol. Biol. Phys. vol. 77, No. 2, 2010, pp. 509-515.
Smith, Benjamin D., et al., "Accelerated partial breast irradiation consensus statement from the american society for radiation oncology (ASTRO)," Int. J. Radiat. Oncol. Biol. Phys., vol. 74, No. 4, 2009, pp. 987-1001.
Veronesi, Umberto, et al., "Twenty year follow-up of a randomized study comparing breast-conserving surgery with radical mastectomy for early breast cancer," N. Engl. J. Med., vol. 347, No. 16, Oct. 17, 2002, pp. 1227-1232.
Jain, Anudh K., et al., "Does three-dimensional external beam partial breast irradiation spare lung tissue compared with standard whole breast irradiation?" Int. J. Radiat. Oncol. Biol. Phys., vol. 75, No. 1, 2009, pp. 82-88.
Recht, Abram, et al., "Lung dose-volume parameters and the risk of pneumonitis for patients treated with accelerated partial-breast irradiation using three-dimensional conformal radiotherapy," J. Clin. Oncol., vol. 27, No. 24, Aug. 20, 2009, pp. 3887-93.
Low, Jennifer A, et al., "Long-term follow-up for locally advanced and inflammatory breast cancer patients treated with multimodality therapy," J. Clin. Oncol., vol. 22, No. 20, Oct. 15, 2004, pp. 4067-4074.
Romond, Edward H., et al., "Trastuzumab plus adjuvant chemotherapy for operable HER2- positive breast cancer," N. Engl. J. Med., vol. 353, No. 16, Oct. 20, 2005, pp. 1673-1684.
Piccart-Gebhart, Martine J., et al., "Trastuzumab after adjuvant chemotherapy in HER2-positive breast cancer," N. Engl. J. Med., vol. 353, No. 16, Oct. 20, 2005, pp. 1659-1672.
Berrington de Gonzalez, A., et al., "Second solid cancers after radiotherapy for breast cancer in Seer cancer registries," Br. J. Cancer 2009, vol. 102, No. 1, Jan. 5, 2010, pp. 220-226.
Stovall, Marilyn, et al., "Dose to the contralateral breast from radiotherapy and risk of second primary breast cancer in the Wecare study," Int. J. Radiat. Oncol. Biol. Phys., vol. 72, No. 4, 2008, pp. 1021-1030.
Kozak, Kevin R., et al., "Dosimetric comparison of two different three-dimensional conformal external beam accelerated partial breast irradiation techniques," Int. J. Radiat. Oncol. Biol. Phys., vol. 65, No. 2, 2006, pp. 340-346.
Rusthoven, Kyle E., et al., "Accelerated partial-breast intensity-modulated radiotherapy results in improved dose distribution when compared with three-dimensional treatment-planning techniques," Int. J. Radiat. Oncol. Biol. Phys., vol. 70, No. 1, 2008, pp. 296-302.
Moran, Jean M., et al., "Accelerated partial breast irradiation: what is dosimetric effect of advanced technology approaches?," Int. J. Radiat. Oncol. Biol. Phys., vol. 75, No. 1, 2009, pp. 294-301.
Wernicke, A.G., et al., "External beam partial breast irradiation following breast-conserving surgery: preliminary results of cosmetic outcome of NYU 00-23," Int. J. Radiat. Oncol. Biol. Phys. vol. 66, No. 3, Supplement, 2006, p. S32.
Formenti, Silvia C., et al., "Prone accelerated partial breast irradiation after breast-conserving surgery: preliminary clinical results and dose-vol. histogram analysis," Int. J. Radiat. Oncol. Biol. Phys., vol. 60, No. 2, 2004, pp. 493-504.
Kozak, Kevin R., et al., "Dosimetric comparison of proton and photon three-dimensional, conformal, external beam accelerated partial breast irradiation techniques," Int. J. Radiat. Oncol. Biol. Phys., vol. 65, No. 5, 2006, pp. 1572-1578.
Yu CX., "Intensity-modulated arc therapy with dynamic multileaf collimation: an alternative to tomotherapy," Phys. Med. Biol., vol. 40, 1995, pp. 1435-1449.
Yu, Cedric X., et al., "Clinical implementation of intensity-modulated arc therapy," Int. J. Radiat. Oncol. Biol. Phys.. vol. 53, No. 2, 2002, pp. 453-463.
Burgess, L., et al., "Partial Brain VMAT Planning Using Simultaneous Couch and Gantry Arcs," Int. L. Radiation Oncology Biol. Phys., vol. 78, Issue 3, Supplement 1, Nov. 1, 2010, pp. S818-S819.
Otto K., "Volumetric modulated arc therapy: IMRT in a single gantry arc," Med. Phys., vol. 35, 2008, pp. 310-317.
Palma, David, et al., Volumetric modulated arc therapy for delivery of prostate radiotherapy: comparison with intensity-modulated radiotherapy and three-dimensional conformal radiotherapy, Int. J. Radiat. Oncol. Biol. Phys., vol. 72, No. 4, 2008, pp. 996-1001.
Duthoy, W., et al., "Clinical implementation of intensity-modulated arc therapy (IMAT) for rectal cancer," Int. J. Radiat. Oncol. Biol. Phys., vol. 60, No. 3, 2004, pp. 794-806.
Lagerwaard FJ., et al., Whole-brain radiotherapy with simultaneous integrated boost to multiple brain metastases using volumetric modulated arc therapy, Int. J. Radiat. Oncol. Biol. Phys., vol. 75, No. 1, 2009, pp. 253-259.
Popescu CC., et al., "Volumetric modulated arc therapy improves dosimetry and reduces treatment time compared to conventional intensity-modulated radiotherapy for locoregional radiotherapy of left-sided breast cancer and internal mammary nodes," Int J Radiat Oncol Biol Phys, vol. 76, No. 1, 2009, pp. 287-295.
Clarke M., et al., "Effects of radiotherapy and of differences in the extent of surgery for early breast cancer on local recurrence and 15-year survival: an overview of the randomised trials," Lancet, vol. 366, 2005, pp. 2087-2106.
Paszat, Lawrence F., et al., "Mortality from myocardial infarction following postlumpectomy radiotherapy for breast cancer. A popu-

(56) References Cited

OTHER PUBLICATIONS lation-based study in Ontario, Canada," Int J Radiat Oncol Biol Phys, vol. 43, No. 4, 1999, pp. 755-762.

Baglan, Kathy L. et al., "Accelerated partial breast irradiation using 3D conformal radiation therapy (3D-CRT)," Int J Radiat Oncol Biol Phys, vol. 55, No. 2, 2003, pp. 302-11.

Pignol, Jean-Philippe, et al., "A multicenter randomized trial of breast intensity-modulated radiation therapy to reduce acute radiation dermatitis," J Clin Oncol, vol. 26, No. 13, May 1, 2008, pp. 2085-2092.

Reeder, Reed, et al., "Predictors for clinical outcomes after accelerated partial breast intensity-modulated radiotherapy," Int J Radiat Oncol Biol Phys, vol. 74. No. 1, 2009, pp. 92-97.

Hall, Eric J., et al., "Radiation-induced second cancers: The impact of 3D-CRT and IMRT," Int J Radiat Oncol Biol Phys, vol. 56, No. 1, 2003, pp. 83-88.

Shaitelman, Simone F., et al., "Continuous Arc Rotation of the Couch Therapy for the Delivery of Accelerated Partial Breast Irradiation: A Treatment Planning Analysis," Int. J. Radiation Oncology Biol. Phys., vol. 80, No. 3, 2011, pp. 771-778.

Takahashi, S., "Conformation Radiotherapy. Rotation Techniques as Applied to Radiography and Radiotherapy of Cancer," Acta Radiol, Diagn (Stockh), Suppl 242:1+, 1965, pp. 11-140.

International Search Report and Written Opinion for International Application No. PCT/US2011/000006, mailed Mar. 1, 2011.

International Search Report for PCT/US2007/012607 dated Apr. 11, 2008, two pages.

* cited by examiner

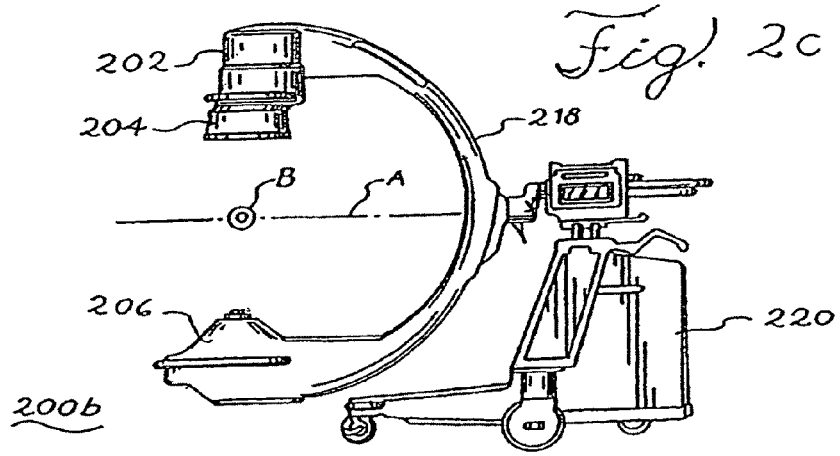
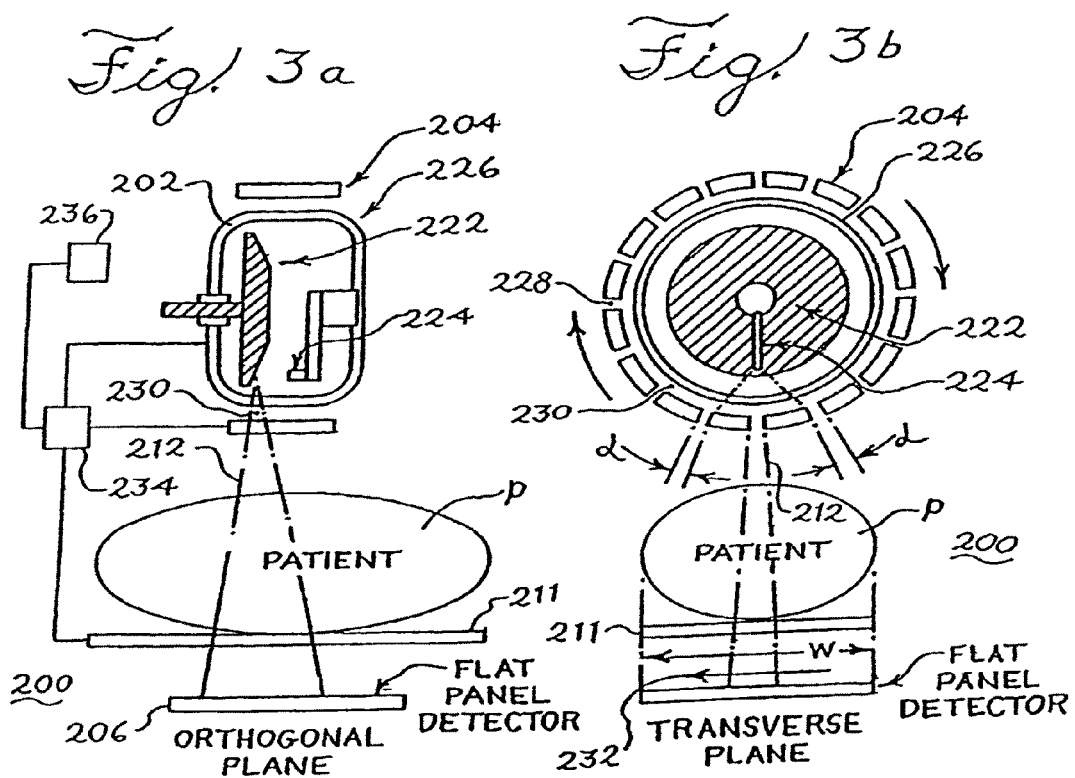

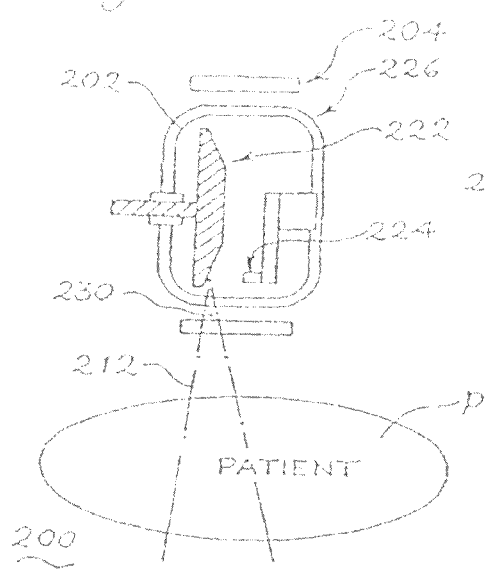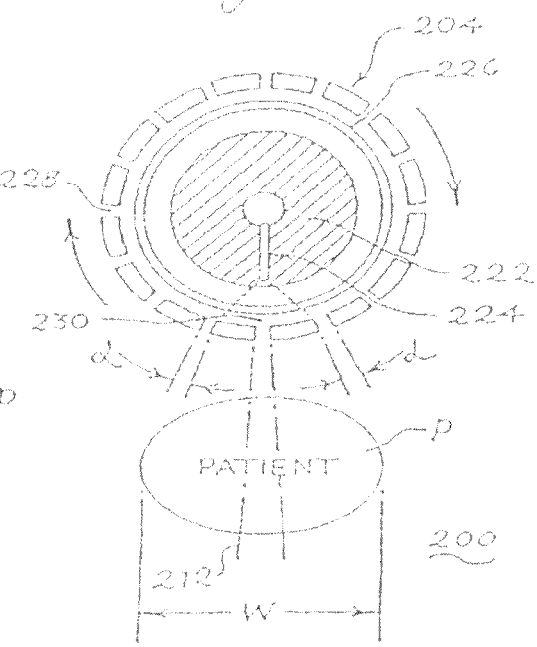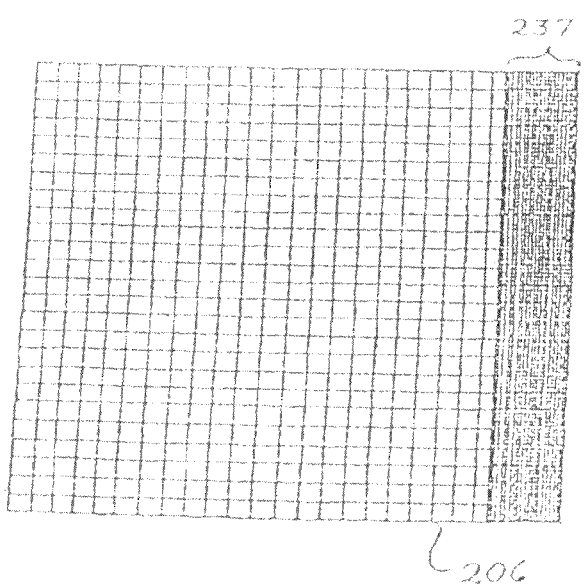

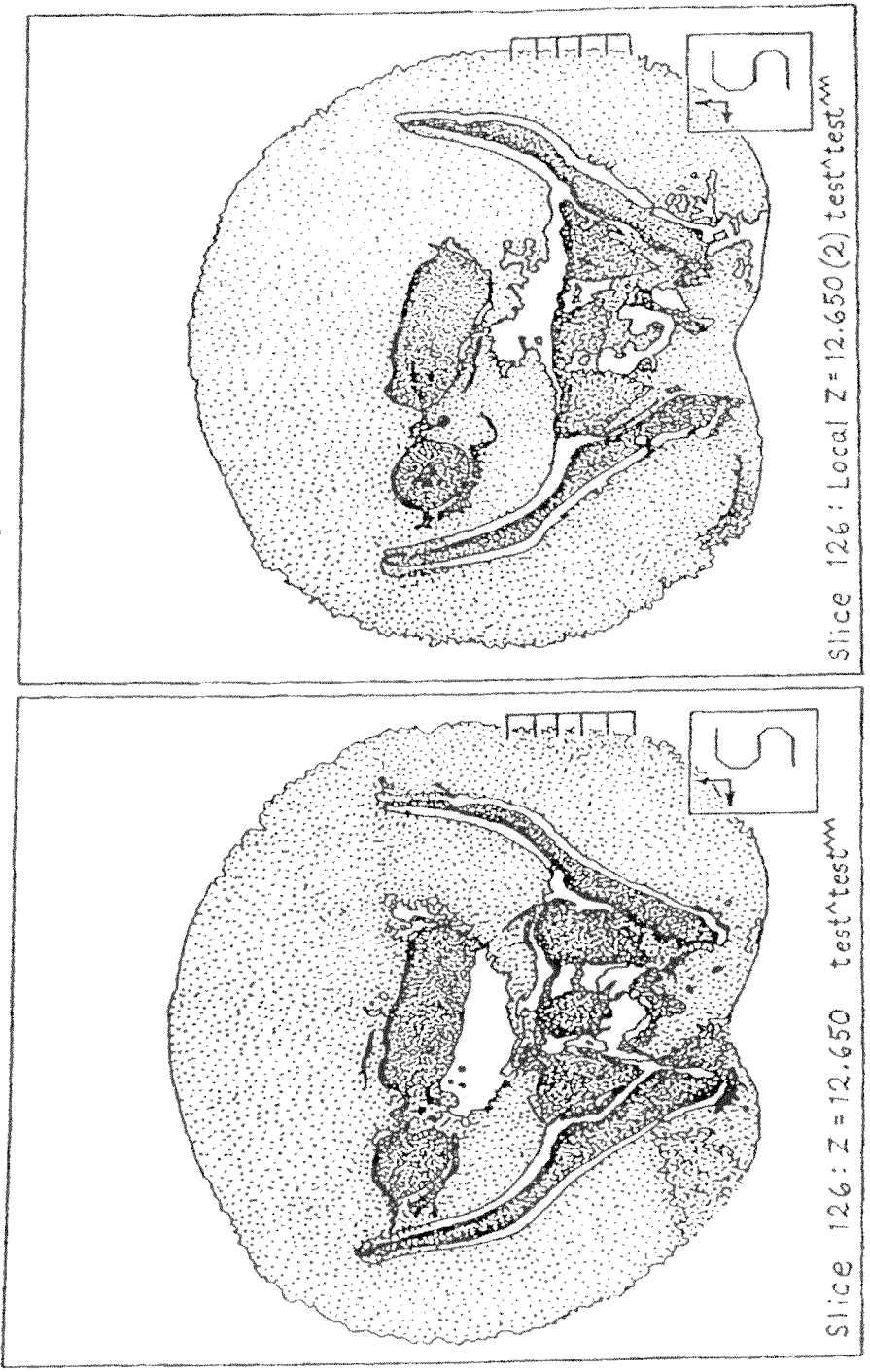

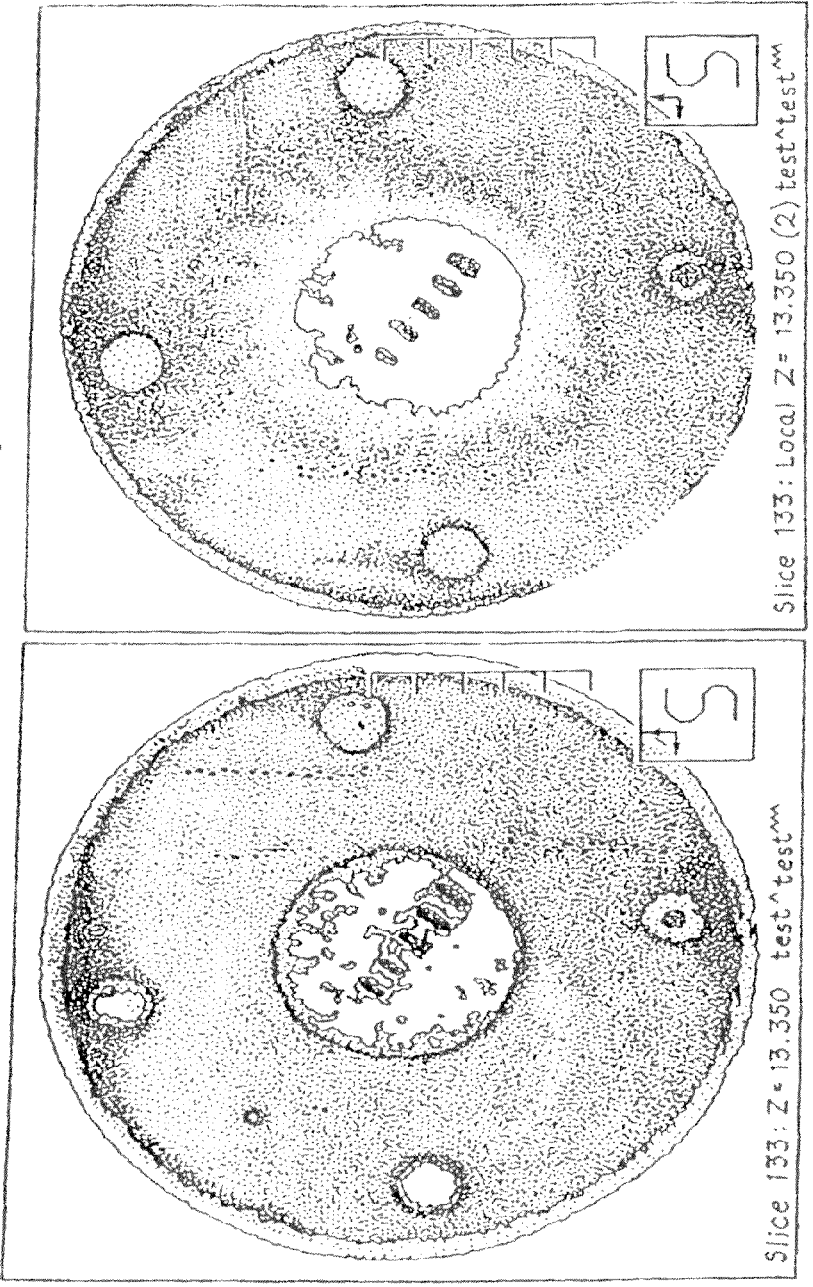

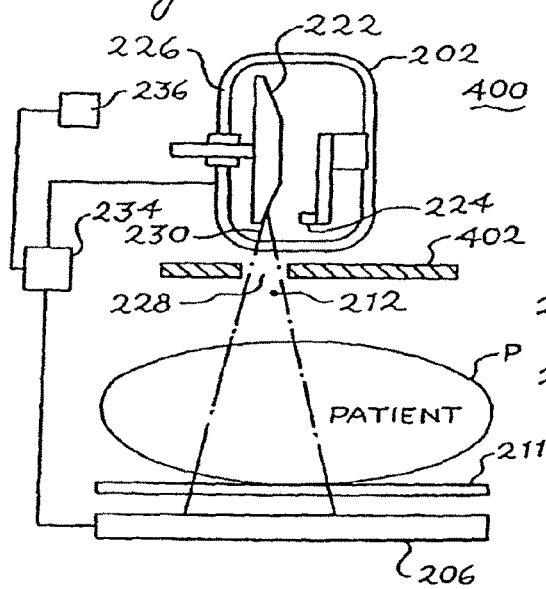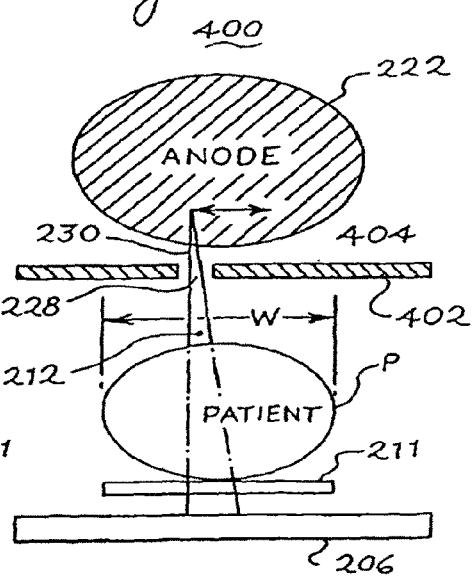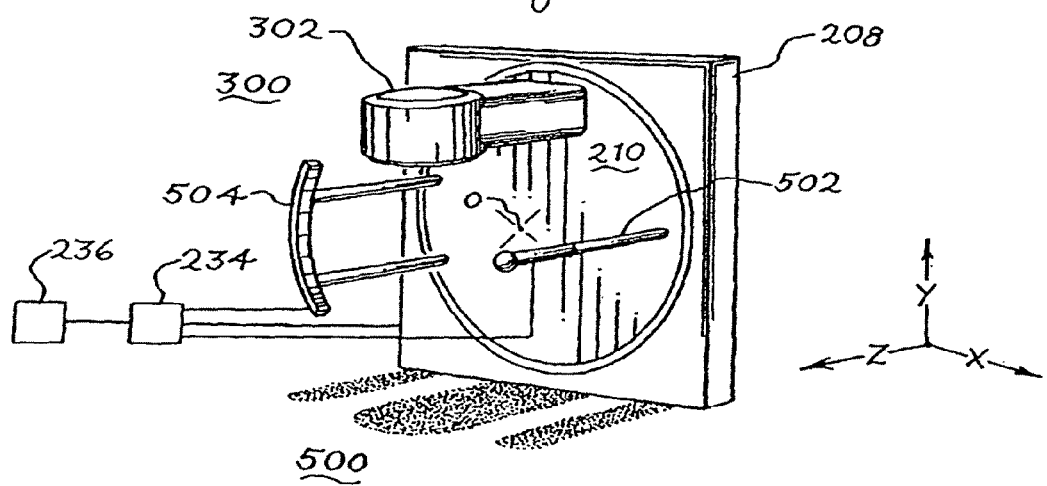

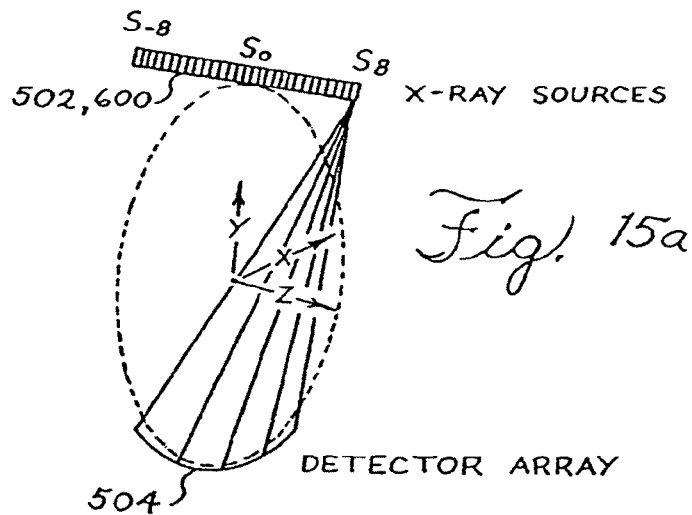
Fig. 15a
Fig. 15b
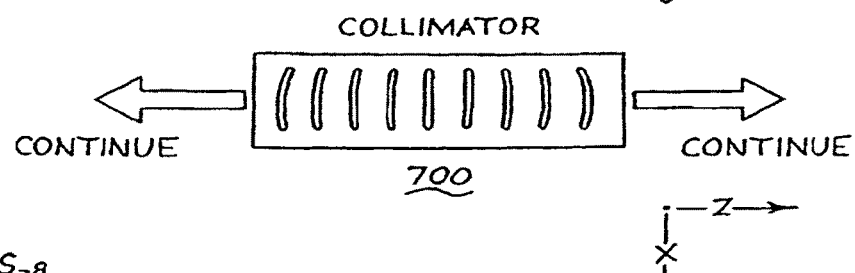
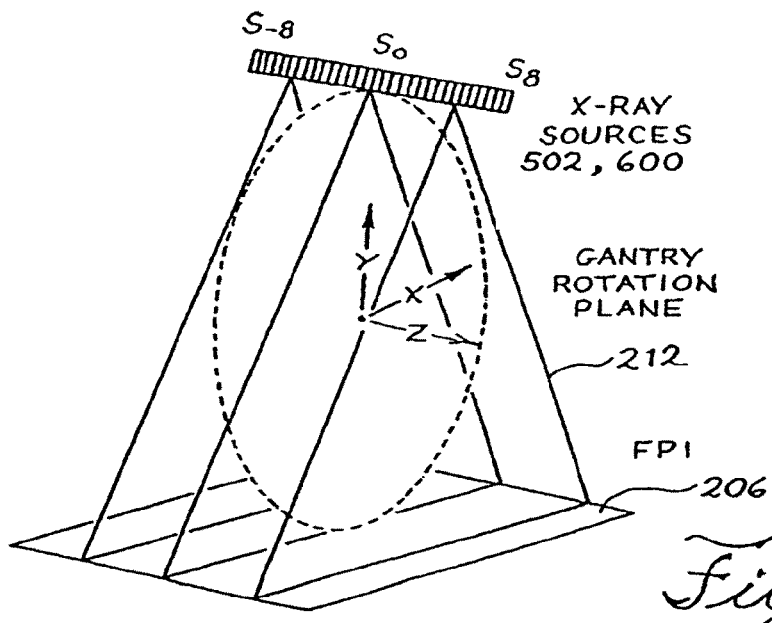
Fig. 16

TETRAHEDRON BEAM COMPUTED TOMOGRAPHY

This application is a continuation application of U.S. patent application Ser. No. 11/786,781, filed Apr. 12, 2007 now U.S. Pat. No. 7,760,849, which claims the benefit of priority of the filing date of Apr. 14, 2006, of U.S. Provisional Patent Application Ser. No. 60/792,207, filed on the aforementioned date, wherein both of the above mentioned U.S. regular and provisional applications are incorporated in their entirety by reference herein.

The inventions described in one or more claims were made with Government support under Grant No. 1R21CA130330-01A1 awarded by the National Institutes of Health. The Government has certain rights in the inventions of such one or more claims.

BACKGROUND OF THE INVENTION

1. Field of the Invention

The present invention relates generally to an imaging system that employs one or more slots to scan an object with x-rays that are used for imaging the object.

2. Discussion of the Related Art

A known x-ray imaging system is an X-ray cone-beam computed tomography system. Mechanical operation of a cone beam computed tomography system is similar to that of a conventional computed tomography system, with the exception that an entire volumetric image is acquired through at most a single rotation of the source and detector. This is made possible by the use of a two-dimensional (2-D) detector, as opposed to the one-dimensional (1-D) detectors used in conventional computed tomography.

An example of a known cone beam computed tomography imaging system is described in U.S. Pat. No. 6,842,502, the entire contents of which are incorporated herein by reference. The patent describes an embodiment of a cone-beam computed tomography imaging system that includes a kilovoltage x-ray tube and a flat panel imager having an array of amorphous silicon detector. As a patient lies upon a treatment table, the x-ray tube and flat panel image rotate about the patient in unison so as to take a plurality of images as described previously.

In cone-beam computed tomography systems, such as the one described above, scatter may be a major cause of reduced image quality. Current techniques for scatter correction or rejection include calculating the scatter and then subtracting the scatter from the signal. However, the length of time the scatter calculation requires can be as long as hours or days using the Monte Carlo method. Furthermore, the noise from the scatter remains after the scatter profile has been subtracted from the signal, such that the signal-to-noise ratio decreases.

In another technique, the scatter is measured and then subtracted from the signal. This technique, however, subjects the patient to additional radiation exposure and prolonged scanning time and requires an additional scan to measure the scatter profile. Further, the noise from the scatter remains, which sacrifices the signal-to-noise ratio.

In yet another technique, a grid is positioned in front of the detector and behind the patient to block some scatter. However, the grid also partially blocks the primary x-ray beams, resulting in additional radiation exposure to the patient. Other techniques use an air gap by increasing the distance from the detector to the patient, which reduces the scatter that is collected by the detector. Because of mechanical limitations, however, the distance from the detector to the patient can be increased only a finite amount.

The images of other imaging systems are known to suffer from the effects of scatter. One such imaging system is digital tomosynthesis system. Digital tomosynthesis operates in the same way as cone-beam computed tomography but reconstructs images differently. Compared to cone-beam tomography, smaller range of projection angles is necessary for digital tomosynthesis.

Another known x-ray imaging system suffering from scatter is a megavoltage electronic portal imaging system. The operation of megavoltage electronic portal imaging system is similar to digital radiography except the x-ray photons have much higher energy. The x-ray source is the radiation treatment beam which is generated by linear accelerator. The detector may be a flat panel detector that comprises of a metal plate, a scintillation screen and charge coupled device (CCD) photodiode array. The metal plate partially converts photon into electrons. The electrons, as well as some photons that pass through the metal plate, yield visible light in scintillation screen. The visible lights are detected by the CCD photodiode array and form an image in a computer display.

Megavoltage portal images are used for patient positioning prior to radiation treatments. However, the quality of megavoltage image is not optimal due to low detection efficiency and scatter. Due to the high x-ray photon energy, most of high energy photons penetrate the metal plate and the scintillation screen without being detected. Low detection efficiency causes an inferior signal-to-noise ratio and, thus, an excessive radiation dose is needed to provide an adequate image of the object. Moreover, as photons pass through the imaged object, they are scattered and may be detected. Scatter photons further decrease image contrast and increase noises in the same way as cone beam computed tomography and digital tomosynthesis.

In cone-beam computed tomography systems, a flat panel detector is usually used for detection of x-ray photons. A flat panel detector may include a scintillation screen and a charge-coupled device photodiode array. The scintillation screen converts x-ray photons into visible light photons. The visible light photons are then detected by photodiode array. The performance of such flat panel detectors, in the aspect of signal-to-noise ratio, detection efficiency, is inferior to discrete x-ray detectors that are used in diagnostic helical computed tomography scanner. High noise level and low detection efficiency cause poor low contrast differentiation and noisier images. A further reduction in image quality may be caused by suboptimal performance of a flat panel imager. Approximate reconstruction artifacts exist when cone angle is large (>5 degrees).

In various conventional cone-beam computed tomography, megavoltage and digital tomosynthesis imaging systems the object being imaged may be subjected to non-uniform penetration of imaging radiation in that thinner parts of the object do not need as intensive imaging radiation as thicker parts. As shown in FIG. 1, such systems 100 (not including megavoltage imaging systems) may include a bow-tie filter 102 to modulate the beam intensity profile 104 across the patient/object 106. The bow-tie filter 102 is a block of x-ray attenuation material thicker outside and thinner in the center. The filter 102 interacts with the cone-beam of x-rays 108 generated by x-ray source 110 so that the beam intensity profile is modulated so that a less intensive x-ray beam is delivered to the thinner part of the imaged object. One disadvantage of such a filter 102 is that the thickness of the imaged object is different for different positions. For example, the thickness of the head of a patient is different from the thickness of the pelvis of the same patient. Also the thickness of the imaged object varies with imaging angles. For example, the pelvis is thinner if imaged in superior-inferior directions than if imaged from lateral directions. Since the intensity profile generated by a bow-tie filter, the current beam intensity modulation using a bow-tie filter does not accommodate different shapes of the imaged object and beam angles.

Accordingly, it is an object of the present invention to reduce scatter generated in a cone-beam computed tomography, digital tomosynthesis and megavoltage portal imaging systems.

Another object of the present invention is to eliminate the need to use a bow-tie filter in cone-beam computed tomography and digital tomosynthesis systems and to dynamically modulate beam intensity based on the shape of the imaged object and the beam angles.

Another object of the present invention to increase detection efficiency of megavoltage portal imaging system.

BRIEF SUMMARY OF THE INVENTION

One aspect of the present invention regards a cone-beam computed tomography system including an x-ray source that emits an x-ray beam, a slot that intercepts the x-ray beam so that a plurality of fan-shaped x-ray beams emanate from the slot towards an object. The system includes a detector receiving fan-shaped x-rays after they pass through the object, the detector generating an imaging signal for each of the received fan-shaped x-rays. A computer is connected to the detector so as to receive the imaging signals for each of the received fan-shaped x-rays, wherein the x-ray source, the slot and the detector rotate about the object so that multiple imaging signals are reconstructed by the computer to generate a three-dimensional cone-beam computed tomography image therefrom. The system further includes a display connected to the computer and displaying the three-dimensional cone-beam computed tomography image.

A second aspect of the present invention regards a method of imaging an object that includes i) emitting from an x-ray source an x-ray beam in a fan-shaped form towards an object, ii) detecting x-rays that pass through the object due to the emitting an x-ray beam with a detector and iii) generating image data of the object from the detected x-rays. The method includes iv) rotating the x-ray source and the detector relative to the object and continuously repeating steps i)-iv) until a sufficient number of imaging data regarding the object is generated so as to form a three-dimensional cone-beam computed tomography image therefrom. The method including forming a three-dimensional cone-beam computed tomography image from the sufficient number of imaging data and displaying the three-dimensional cone-beam computed tomography image.

A third aspect of the present invention regards a method of imaging an object that includes directing a plurality of x-ray beams in a fan-shaped form towards an object, detecting x-rays that pass through the object due to the directing a plurality of x-ray beams and generating a plurality of imaging data regarding the object from the detected x-rays. The method further includes forming a three-dimensional cone-beam computed tomography image from the plurality of imaging data and displaying the three-dimensional cone-beam computed tomography image.

A fourth aspect of the present invention regards a digital tomosynthesis system including an x-ray source that emits an x-ray beam and a slot that intercepts the x-ray beam so that a plurality of fan-shaped x-ray beams emanate from the slot towards an object. The system further includes a detector receiving fan-shaped x-rays after they pass through the object, the detector generating an imaging signal for each of the received fan-shaped x-rays. A computer is connected to the detector so as to receive the imaging signals for each of the received fan-shaped x-rays, wherein the x-ray source, the slot and the detector rotate about the object so that multiple imaging signals are reconstructed by the computer to generate a digital tomosynthesis image therefrom. The system further includes a display connected to the computer and displaying the digital tomosynthesis image.

A fifth aspect of the present invention regards a method of imaging an object that includes i) emitting from an x-ray source an x-ray beam in a fan-shaped form towards an object and ii) detecting x-rays that pass through the object due to the emitting an x-ray beam with a detector. The method further includes iii) generating image data regarding the object from the detected x-rays and iv) rotating the x-ray source and the detector relative to the object and continuously repeating steps i)-iv) until a sufficient number of imaging data regarding the object is generated so as to form a digital tomosynthesis image therefrom. The method further includes forming a digital tomosynthesis image from the sufficient number of imaging data and displaying the digital tomosynthesis image.

A sixth aspect of the present invention regards a quasi-cone-beam computed tomography system that includes an x-ray source that sequentially emits a plurality of x-ray beams at different positions along a scanning direction and a collimator that intercepts the plurality of x-ray beams so that a plurality of fan-shaped x-ray beams emanate from the collimator towards an object. The system includes a detector receiving fan-shaped x-rays after they pass through the object, the detector generating an imaging signal for each of the received fan-shaped x-rays. A computer is connected to the detector so as to receive the imaging signals for each of the received fan-shaped x-rays, wherein the x-ray source, the slot and the detector rotate about the object so that multiple imaging signals are reconstructed by the computer to generate a three-dimensional cone-beam computed tomography image therefrom. The system further includes a display connected to the computer and displaying the three-dimensional cone-beam computed tomography image.

A seventh aspect of the present invention regards a method of imaging an object that includes i) emitting from an x-ray source a plurality of x-ray beams at different positions along a scanning direction and ii) forming a plurality of fan-shaped x-ray beams from the plurality of x-ray beams emitted from the x-ray source. The method further includes ii) detecting x-rays that pass through the object due to the emitting an x-ray beam with a detector and iii) generating image data regarding the object from the detected x-rays. The method including iv) rotating the x-ray source and the detector relative to the object and continuously repeating steps i)-iv) until a sufficient number of imaging data regarding the object is generated so as to form a three-dimensional cone-beam computed tomography image therefrom. The method further including forming a three-dimensional cone-beam computed tomography image from the sufficient number of imaging data and displaying the three-dimensional cone-beam computed tomography image.

An eighth aspect of the present invention regards a linear scanning system that includes an x-ray source that sequentially emits a plurality of x-ray beams at different positions along a scanning direction, wherein the x-ray source has an anode and a single cathode aligned along the scanning direction, wherein electrons are emitted from different areas of the single cathode so as to strike areas of space occupied by the anode that correspond to the different positions. The system further includes a controller to control the x-ray source to sequentially emit the plurality of x-ray beams at the different positions along the scanning direction.

A ninth aspect of the present invention regards a method of scanning that includes sequentially forming x-ray beams off of different areas of an anode of an x-ray source and sequentially forming x-ray beams off of the different areas of the anode by sequentially directing electrons from a single cathode of the x-ray source towards the different areas.

A tenth aspect of the present invention regards a scanning system that includes an x-ray source that sequentially emits a plurality of x-ray beams at different positions along a scanning direction, wherein the x-ray source has an anode and a cathode system aligned along the scanning direction, wherein electrons are emitted from different areas of the cathode system so as to strike areas of space occupied by the anode that correspond to the different positions. The system further including a controller to modulate intensities of each of the plurality of x-ray beams by modulating a current of the electrons striking the anode.

An eleventh aspect of the present invention regards a method of scanning that includes generating a plurality of x-ray beams that strike different areas of an object and modulating intensities of each of the plurality of x-ray beams by modulating a current of particles striking a target that generate the plurality of x-ray beams.

A twelfth aspect of the present invention regards a megavoltage imaging system that includes a megavoltage x-ray source that emits an x-ray beam having a range of energies therein that range from 0 to 4 MV and a slot that intercepts the x-ray beam so that a plurality of fan-shaped x-ray beams emanate from the slot towards an object. The system further includes a detector receiving fan-shaped x-rays after they pass through the object, the detector generating an imaging signal for each of the received fan-shaped x-rays and a computer connected to the detector so as to receive the imaging signals for each of the received fan-shaped x-rays. A display is connected to the computer and displays an image of the object based on the imaging signals.

A thirteenth aspect of the present invention regards a method of imaging an object that includes directing a plurality of x-ray beams in a fan-shaped form towards an object, wherein each of the plurality of x-ray beams has a range of energies therein that range from 0 to 4 MV. The method includes detecting x-rays that pass through the object due to the directing a plurality of x-ray beams and generating a plurality of imaging data regarding the object from the detected x-rays. The method further includes forming an image from the plurality of imaging data and displaying the image.

One or more aspects of the present invention provide the advantage of rejecting scatter without the loss of the signal-to-noise ratio or additional radiation exposure to patient.

One or more aspect of the present invention provides the advantage of modulating beam intensity across a patient to avoid artifacts and to minimize the radiation dose the patient receives.

Additional objects, advantages and features of the present invention will become apparent from the following description and the appended claims when taken in conjunction with the accompanying drawings.

BRIEF DESCRIPTION OF THE DRAWINGS

FIG. 2c is a side view of a third embodiment of a scanning slot cone-beam computed tomography system in accordance with the present invention;

FIGS. 3a and c depict a cross-sectional view of the scanning slot cone-beam computed tomography system of FIG. 2 taken in a plane perpendicular to a scanning direction in accordance with an embodiment of the present invention;

FIGS. 3b and d depict a cross-sectional view of the scanning slot cone-beam computed tomography system of FIG. 2 taken in a plane transverse to the plane of FIGS. 3a and c;

FIG. 4 depicts an embodiment of a flat panel matrix detector for scanning readout mode for the cone-beam computed tomography systems of FIGS. 2a-c in accordance with the present invention;

FIGS. 5a and 5b show a comparison of the image quality from a conventional cone-beam computed tomography system (FIG. 5a) and from the scanning slot beam computed tomography system of FIGS. 2a and 3a-d (FIG. 5b);

FIGS. 7a and 7b further show a comparison of the image quality from the scanning slot beam computed tomography system of FIGS. 2a and 3a-d (FIG. 7a) and from the conventional cone-beam computed tomography system cone beam system (FIG. 7b);

FIG. 9a depicts a cross-sectional view of a scanning focus spot cone-beam computed tomography system taken in a plane perpendicular to a scanning direction in accordance with another embodiment of the present invention;

FIG. 9b depicts a cross-sectional view of the scanning focus spot cone-beam computed tomography system of FIG. 7a taken in a plane transverse to the plane of FIG. 9a;

FIG. 10 schematically shows an embodiment of a quasi-cone-beam computed tomography system used in conjunction with a radiotherapy source in accordance with the present invention;

FIG. 11b schematically shows a front cross-sectional view of the x-ray source of FIG. 11a;

FIGS. 15a-b schematically show a configuration using a linear x-ray source and curved slot collimator with the systems of FIGS. 10-14; and FIG. 16 shows a flat panel imager to be used with the systems of FIGS. 10-14.

PREFERRED EMBODIMENTS OF THE INVENTION

Figure 2A:
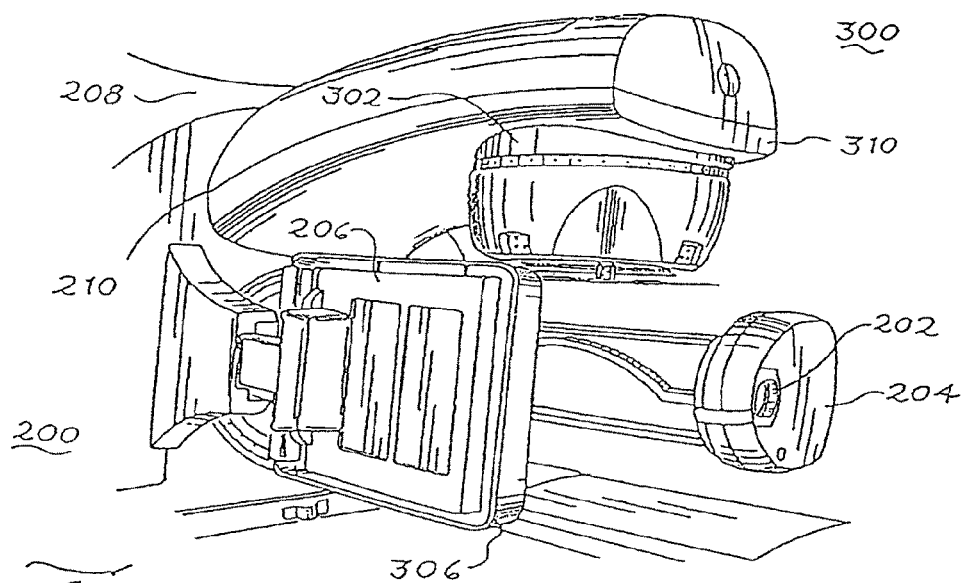
FIG. 2a is a perspective view of a first embodiment of a scanning slot cone-beam computed tomography system and a first embodiment of a megavoltage portal imaging system used in conjunction with a radiotherapy source in accordance with the present invention.

Referring now to FIGS. 2-16, various imaging systems embodying the principles of the present invention are illustrated, wherein like elements are denoted by like numerals. In particular, FIG. 2a shows an embodiment of a wall-mounted scanning slot cone-beam computed tomography system 200 and megavoltage portal imaging system 300 that can be adapted to be used with the cone-beam computed tomography and megavoltage portal imaging system sold under the tradename Synergy by Elekta of Crawley, the United Kingdom. The system 200 may be retrofitted onto an existing or new radiation therapy system that includes a separate radiation therapy x-ray source. The cone-beam computed tomography system 200 includes an x-ray source, such as x-ray tube 202, a rotary collimator 204 and a flat-panel imager/detector 206 mounted on a gantry 208.

As shown in FIG. 2a, the flat-panel imager 206 can be mounted to the face of a flat, circular, rotatable drum 210 of the gantry 208 of a medical linear accelerator 302, where the x-ray beam 212 produced by the x-ray tube 202 is approximately orthogonal to the treatment beam 304 produced by the radiation therapy source 302. Note that an example of mounting of an x-ray tube and an imager to a rotatable drum is described in U.S. Pat. No. 6,842,502, the entire contents of which are incorporated herein by reference.

As shown in FIGS. 2a and 3, the system 300 includes a separate radiation therapy x-ray source, such as a linear source 302, and a detector 306 that are separately mounted to the rotating drum 210. The source 302 operates at a power level higher than that of x-ray tube 202 so as to allow for treatment of a target volume in a patient lying on movable table 211 (movable in x, y and z-direction via computer 234). The linear source 302 generates a beam 304 of either photons, such as x-rays, or particles, such as electrons, which have an energy ranging from 4 MeV to 25 MeV.

Figure 2B:
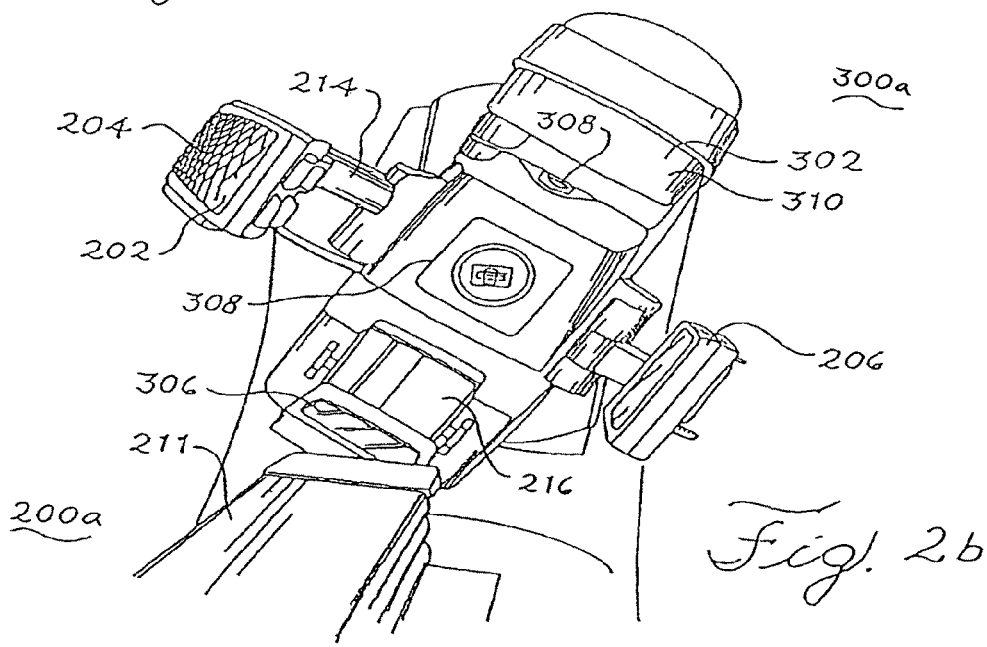
FIG. 2b is a front perspective view of a second embodiment of a scanning slot cone-beam computed tomography system and a second embodiment of a megavoltage portal imaging system used in conjunction with a radiotherapy source in accordance with the present invention.

Another embodiment of a scanning slot cone-beam computed tomography system 200a and megavoltage portal imaging system 300a is shown in FIG. 2b. In this embodiment, the system 200a and system 300a can be adapted to be used with the cone-beam computed tomography and megavoltage portal imaging system sold under the tradename Trilogy by Varian Medical Systems of Palo Alto, Calif. The system 200a includes an x-ray tube 202, a rotary collimator 204 and a flat-panel imager/detector 206 similar to those used in the embodiment of FIG. 2a. Unlike the system 200 mounted on a drum, the x-ray tube 202 and collimator 204 are mounted on an arm 214 pivotably mounted to a support 308 of the system 300a. Similarly, the flat panel imager 206 is mounted on an arm 216 mounted to the support 308.

As with the embodiment of FIG. 2a, the x-ray beam 212 produced by the x-ray tube 202 of FIG. 2b is approximately orthogonal to the treatment beam 304 produced by the radiation therapy source 302. As shown in FIGS. 2b and 3, the system 300a includes a linear source 302 and detector 306 similar to those described previously with respect to FIG. 2a. Accordingly, the linear source 302 generates a beam 304 of either photons, such as x-rays, or particles, such as electrons, which have an energy ranging from 4 MeV to 25 MeV so as to allow for treatment of a target volume in a patient lying on movable table 211 (movable in x, y and z-directions via computer 234). Unlike the system 300 mounted on a drum, the linear source 302 and the detector 306 are connected with support 308.

Another embodiment of a scanning slot cone-beam computed tomography system 200b is shown in FIG. 2c. In this embodiment, the system 200b includes a kilo-voltage x-ray tube 202, a rotary collimator 204 and a flat-panel imager/detector 206 similar to those used in the embodiment of FIG. 2a. Unlike the system 200 mounted on a drum, the x-ray tube 202 and collimator 204 are mounted at one end of a C-arm 218 while the flat panel imager 206 is mounted at the other end of the C-arm 218. The C-arm 218 is mounted to a movable base 220 so that it can pivot about axes A and B shown in FIG. 2c. The C-arm 218 and base 220 are similar to those of various well known cone-beam computed tomography imaging systems.

While the discussion to follow will describe the scanning slot cone-beam computed tomography system 200 and megavoltage portal imaging system 300 of FIG. 2a, the discussion will be equally applicable to the scanning slot cone-beam computed tomography and megavoltage portal imaging systems of FIGS. 2b-c.

As shown in FIGS. 3a-d, the x-ray source 202 of the scanning slot cone-beam computed tomography system 200 of FIG. 2a includes a rotary anode 222 and a stationary cathode 224 enclosed in a glass housing 226, which in turn is positioned within a rotary collimator 204 that includes a plurality of slots 228. Note that in an alternative embodiment, the rotary collimator 204 can be replaced by a rectangular slot that moves back and forth in a direction parallel to the tangential direction of the collimator 204 in order to reproduce the same scanning action as collimator 204.

When the system 200 is in use, the cathode 224 emits electrons at the anode 222, which is typically made of tungsten or molybdenum. As the electrons strike a single area of space occupied by the anode 222, the tungsten or molybdenum atoms emit X-rays as a beam 230. The x-rays can be in the kV energy range. The beam 230 emanates towards the rotary collimator 204. As shown in FIGS. 3b and 3d, the slots 228 preferably are spaced equidistantly from one another and each defines a rectangular area have dimensions of 2 by 15 cm, wherein the width of 2 cm is measured along the scanning direction. Of course, other dimensions for the rectangular slot are possible depending on the desired size of the beam.

In operation, the width of beam 230 is greater than the width, d, of each slot 228 as shown in FIGS. 3b and 3d. As the beam 230 interacts with and is intercepted by a slot 228, the slot 228 shapes the X-ray conical beam 230 into a fan or slot beam 212 that scans across the detector 206 prior to the components enclosed in the glass housing 226, the collimator 204, and the detector 206 rotating about the patient P via rotation of drum 210. In particular, as the slot 228 rotates, the slot 228 intercepts different portions of the beam 230 so that a plurality of fan beams 212 emanate from the slot 228 so as to scan across a width W of the patient. As shown in FIGS. 3b and 3d, during the imaging of the patient P, the fan beams 212 of X-rays scan or sweep across the patient P from right to left in the transverse plane as indicated by the arrow 232 to create a two-dimensional image at the detector 206. Of course, the system 200 can be arranged such that the beams 212 scan from left to right. Hence, the system 200 can be referred to as a scanning slot cone beam computed tomography system.

As shown in FIG. 4, the host computer 234 synchronizes the area 237 read from the detector 206 based on the electron beam placement from the cathode 224 (and the generated x-ray beam), the rotation of the collimator 204 and the size of the slots 228 so that the area 237 corresponds to the area the beam 212 would intersect if the patient were absent. Obviously, the detector 206 reads out only the region where the detector is radiated with the primary beam, as indicated by the darkened region 237. Of course, the whole image can be read out and the signal outside the area 237 can be discarded. An imaging signal corresponding to the read out region is sent from detector 206 to computer 234. Any scatter present outside of region 237 is not detected. Therefore, there is less data to analyze as compared to when the entire detector is flooded by a conventional cone beam, resulting in faster readout. As the collimator 204 rotates another fan beam 212 is generated as described above and impinges on an adjacent section 236 of the flat panel detector 206. The process continues until the entire detector 206 has received radiation from the fan beams 212. The fan beams 212, when combined, define a cone beam from which a two-dimensional projection is generated by the detector 206. Thus, the imaging signals corresponding to the radiation read out for each of the fan beams 212 by the entire detector 206 after a full scan across the width W of the patient by the fan-shaped beams 212 is used by host computer 234 to generate a two-dimensional projection in a manner similar to that described previously with cone beam computed tomography.

During continuous cone-beam tomography or tomosynthesis scans, the drum 210 (FIG. 2a), support 308 (FIG. 2b) or C-arm 218 (FIG. 2c) rotates with finite speed. Each fan beam 212 has slightly different projection angles, which causes small amount of distortion if they combined into a two dimensional images. It is preferable to use the actual projection angle of each fan beam 212 in cone-beam tomography or tomosynthesis image reconstruction to avoid distortion.

Note that the detector 206 can be composed of a two-dimensional array of semiconductor sensors that may be each made of amorphous silicon (α-Si:H) and thin-film transistors. The analog signal from each sensor is integrated and digitized. The values are transferred to the host computer 234, wherein an image is generated based on the values and shown on display 236 as shown in FIG. 3a. The detector 206 can also include a scintillation screen to convert the received x-rays into visible light which is then detected by a two-dimensional array of detectors.

After the fan beams 212 traverse the width W of the patient and impinge on the entire detector 206 in the manner described above, the computer 234 instructs the drum 210 to rotate causing the x-ray source 202, the collimator 204 and the detector 206 rotate about the patient P to another position so that the scanning process described above can be repeated and another two-dimensional projection is generated. The above rotation of the x-ray source 202, collimator 204 and detector 206 is continued until a sufficient number of two-dimensional images are acquired for forming a cone-beam computed tomography image. At most one full rotation should be needed for this purpose (it is envisioned that images formed from a rotation of less than 360° can be formed as well). The two-dimensional projections from each position are combined in the computer 234 to generate a three-dimensional image to be shown on display 236 in a manner similar to that of the cone-beam computed tomography systems described previously.

While the above described embodiment for the collimator 204 to be used with systems 200, 200a and 200b is rotary, a linear moving collimator can be used instead. Such a collimator would contain one or more rectangular slots and the collimator would move back and forth along a plane. The combination of the slots and movement of the collimator will produce fan beams that will scan the patient in a manner similar to that described previously.

In an alternative and preferred way of forming the image, the fan beams 212 are not combined by the computer 234 to generate a two-dimensional projection prior to forming the three-dimensional image. Instead, the data read for each fan beam 212 generated at each position of the drum 210 is combined directly to generate the three-dimensional image. Such image generation produces less distortion than that described previously.

One particular feature of the system 200, as well as other embodiments of the present invention described below, is the capability of rejecting scatter without the loss of the signal-to-noise ratio (SNR) or additional radiation exposure to patient. Further, as discussed later, the system 200 can also modulate the beam intensity across the patient to avoid artifacts and to minimize the radiation dose the patient receives.

Figures 6A, 6B:
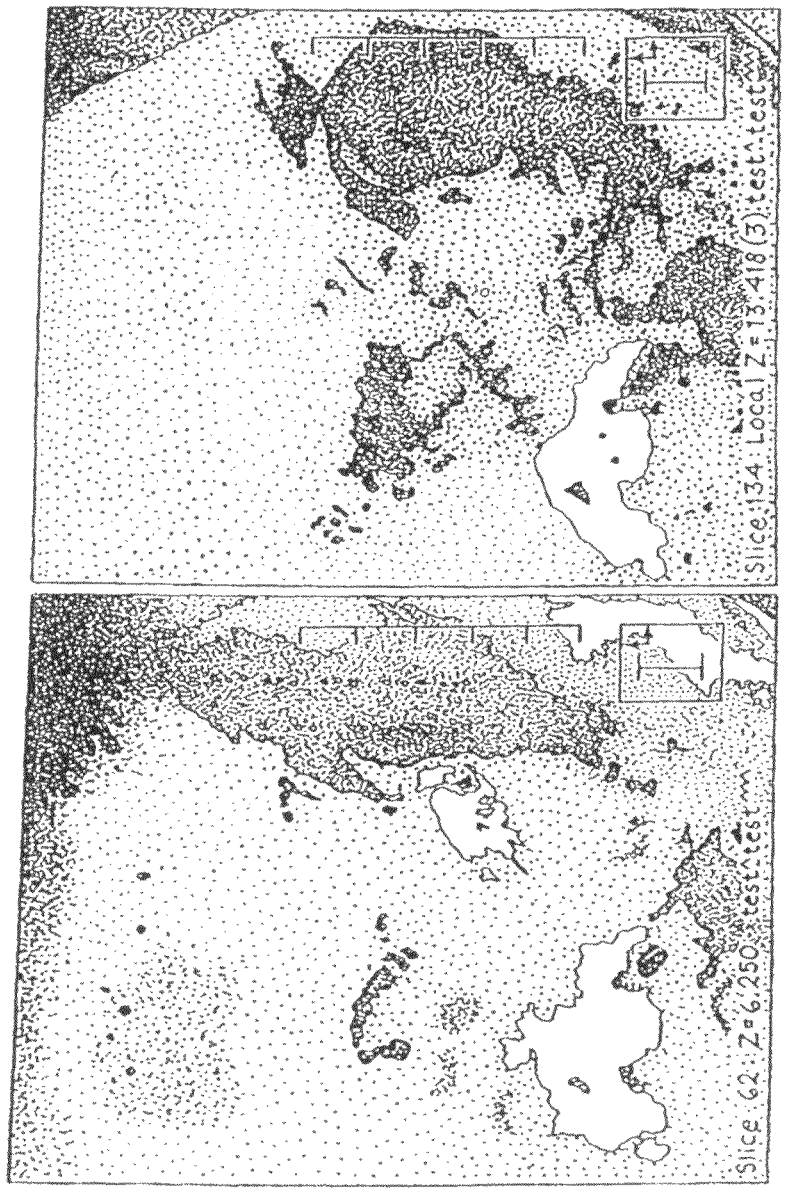
FIGS. 6a and 6b further show a comparison of the image quality from the conventional cone-beam computed tomography system (FIG. 6a) and from the scanning slot beam computed tomography system of FIGS. 2a and 3a-d (FIG. 6b)

Various comparisons between the image quality obtained with slot cone beam computed tomography and with conventional cone beam computed tomography are shown in FIGS. 5 through 7. As is readily seen, the image quality is significantly better with the slot cone beam computed tomography. For example, FIG. 5a shows an image formed from a single cone beam generated from a 15×15 cm collimator while FIG. 5b shows an image of the same object generated by the present invention using a beam of a width of 1.5 cm. FIG. 6a also shows an image formed from a single cone beam generated from a 15.times.15 cm collimator while FIG. 6b shows an image of the same object generated by the present invention using a beam of a width of 2 cm and length of 15 cm. FIG. 7a shows that scatter from a 20 cm diameter phantom using the present invention is less than that generated from a single cone beam interacting with the same phantom as shown in FIG. 7b. FIGS. 5-7 show that the images generated by the system 200 are adequate for computer 234 to control the positioning of the radiation source 202 to direct radiation accurately to a desired area of interest of the patient.

While the previous descriptions of the imaging systems 200, 200a and 200b of FIGS. 2a-c regard the formation of cone-beam tomographic images, the imaging systems 200, 200a and 200b can be altered to generate digital tomosynthesis images. The only difference is that the computer 234 includes software that takes the image data from each of the fan beams and reconstructs them in a well known manner that is different than that of cone-beam computed tomography. The use of collimator 204 reduces scatter in the digital tomosynthesis images.

Now referring to FIGS. 3a-d, as the fan beams sweeps across the imaged object, its intensity can be dynamically modulated and generate a non-uniformed beam intensity profile similar to that from a physical bow-tie filter. Furthermore, the x-ray intensity profile can be modulated based on the shape of the imaged object. Furthermore, the x-ray intensity profile can be modulated based on the x-ray projection angle and the shape of the imaged objection.

One particular feature of the system 200, as well as other embodiments of the present invention described below, is the capability of rejecting scatter without the loss of the signalto-noise ratio (SNR) or additional radiation exposure to patient. Further, as discussed later, the system 200 can also modulate the beam intensity across the patient to avoid artifacts and to minimize the radiation dose the patient receives.

As described previously either a rotary collimator (see FIGS. 3a-d) or a linearly moving slot collimator can be used to reduce scatter in the cone-beam tomographic images or the digital tomosynthesis images formed by systems 200, 200a and 200b. Such collimators can be used to reduce scatter in the megavoltage portal imaging systems 300 and 300a of FIGS. 2a-b. Such portal imaging systems preferably direct electrons having energies of about 4 MeV to strike a target to produce a x-rays that have energies that range from 0 to 4 MV. The x-rays are used to generate a single image of the object/patient.

Figure 8A:
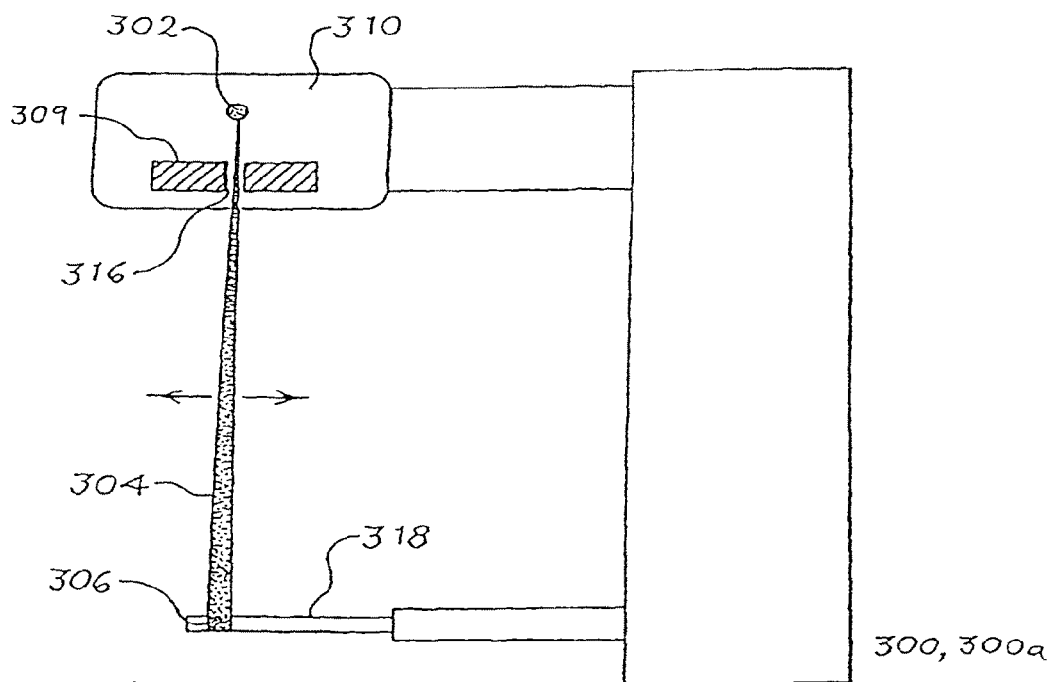
FIG. 8a schematically shows an embodiment of a megavoltage portal imaging system to be used with the megavoltage portal imaging systems of FIGS. 2a-b in accordance with the present invention.
Figure 8B:
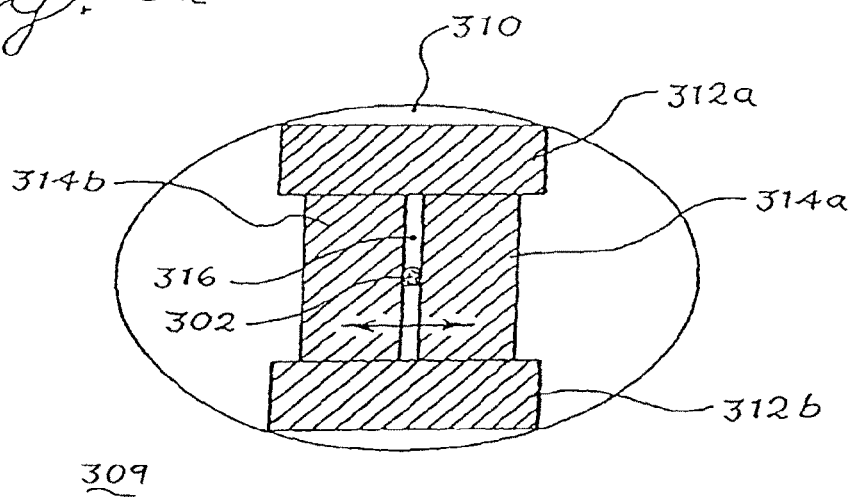
FIG. 8b schematically shows an embodiment of a collimator to be used with the megavoltage portal imaging system of FIG. 8a in accordance with the present invention.

An example of a collimator that can be used with systems 300 and 300a is shown in FIGS. 8a-b. The dynamic collimator 309 is contained within machine head 310 of the systems 300 and 300a.

As shown in FIG. 8b, the collimator 309 includes a pair of stationary collimator jaws 312a, b that are made of an x-ray attenuating/absorbing material such as lead. The collimator 309 further includes a pair of collimator jaws 314a, b that are made of an x-ray attenuating/absorbing material. The jaws 312a, b and 314a, b define a rectangular slot 316. Since the jaws 314a, b move in unison back and forth (see double arrow of FIG. 8b), the slot 316 is constant in area and moves back and forth (see double arrow of FIG. 8a) so as to have a fan-shaped beam 304 scan the patient. The imager 306, can be a flat panel imager or one or more rows of individual detectors, which are laterally movable via linearly movable arm 318, which intercepts the beam 304 so that an image is formed.

As mentioned previously, the detector 306 can be a two dimensional flat panel detector similar imager 206 of systems 200, 200a, 200b. Accordingly, as the slot 316 scans across the field, a plurality of fan beams 304 are directed through the patient onto the imager 306. As with imager 306, any radiation detected outside the area defined by the beam 304 is rejected so that a two-dimensional portal image with minimal scatter is formed.

The detector 306 is preferably a single or multi-row discrete detector array, wherein each detector has a scintillator and a photodiode. The discrete detector can have much better detection efficiency than the previously mentioned flat panel imager. This is due to the thickness of scintillators can be greatly larger than the thickness of scintillation screen. Thus, higher detection efficiency can be achieved.

The detector array can be a single, linear row of detectors. It is, however, preferable that the row be curved so that all detectors focus onto the megavoltage x-ray source 302.

In operation, the single or multi-row detector array does not cover the whole field-of-view that the slot 316 will scan. The detector will move in concert with the slot so that the primary photons of the fan beam 304 are always detected if patient P is not present.

A precisely controlled linear actuator 318 will be used to move the detector array 306. The detector array 306 is preferable to move in the patient's axial direction, either head to toe or toe to head. Of course the detector array 306 can also move left to right or left to right.

Turning now to FIGS. 9a-b, there is schematically shown a scanning focus spot cone beam computed tomography system 400 in accordance with another embodiment of the present invention. The system 400 includes an x-ray source 202 with a rotary anode 222 and a fixed cathode 224. The cathode 224 may include a metallic filament that generates electrons via thermal emission. The rotary anode 222 is made of a material that generates x-rays when struck by electrons, such as tungsten or molybdenum. A fixed collimator 402 is positioned either inside or outside the glass housing 226 of the x-ray source 202. While the collimator 402 shown in FIGS. 9a-b contains a single slot 229, it can contain a plurality of slots, wherein each slot is associated with one of the areas of the anode 222 struck by the electrons.

The focus spot of the electron beam from the cathode 224 on the anode 222 is moved back and forth, as indicated by the double arrow 404, by deflecting the electron beam with a magnetic or electric field. The magnetic or electric field is controlled by a controller or a controller within computer 234. The electron beam strikes multiple, discrete areas of space occupied by the anode 222. In the alternative, the electron beam can strike a continuous area. The fixed collimator 402 shapes the X-ray beams from the anode 222 into a slot or fan-shaped beam 212, which sweeps across the patient as the focus spot is moved back and forth. In particular, as the cathode 224 emits electrons they are directed to a first area of the surface of the anode 222 from which an initial X-ray beam 230 is generated and is directed at a first direction toward a rectangular slot 229 of the collimator 402. A first fan beam 212 is then directed toward a portion of the patient. A second fan beam 212 is generated by having the electrons from the cathode 224 directed to a second area of the area of the anode 222. The above process is continued so that a plurality of fan beams 212 are generated that scan across a width W of the patient. During the imaging of the patient P, the fan beams 212 of X-rays scan or sweep across the patient P from right to left in the transverse plane to create a 2-D image at the detector 206 in a manner similar to that described previously with respect to the embodiment of FIGS. 3a-d. Of course, the system 400 can be arranged such that the beams 212 scan from left to right. Also, the two-dimensional detector 206 can be replaced with a one-dimensional detector that moves so as to track the fan beams 212 that scan across the patient P and generates a two-dimensional image in the manner described previously with the embodiment of FIGS. 3a-d. Hence, the system 400 can be referred to as a scanning focal spot cone beam computed tomography system.

Note that the x-ray source 202, collimator 402 and detector 206 and variations thereof described above can replace the x-ray source 202, collimator 204 and detector 206 of the computed tomography and digital tomosynthesis systems 200, 200a and 200b of FIGS. 2a-c. The generation of images by such systems is performed in a manner similar to that described previously with respect to the embodiment of FIGS. 2-3.

Another approach to improving image quality by reducing scatter is to employ a quasi-cone-beam computed tomography system in accordance with another aspect of Applicant's invention. In this aspect, the systems 200, 200a and 200b of FIGS. 2a-c are essentially altered by 1) replacing the x-ray source 202 with a multi-beam x-ray source as will be described below and 2) replacing flat panel imager/detector 206 with a multi-row detector having a curved shape. Such a quasi-cone-beam computed tomography system 500 is schematically shown in FIG. 10. In particular, the system 500 includes a linear multi-beam x-ray source 502 and a multi-row discrete scintillator/photodiode detector array 504. The array 504 can be constructed from photodiode/scintillator array modules with data acquisition units, which are well known in the art. When adapted to be used with system 200 of FIG. 2a, the x-ray source 502 and detector array 504 are mounted on rotating drum 210 so as to be aligned perpendicular to (source 502) and within (array 504) the rotation plane defined by the drum 210.

Figure 11A:
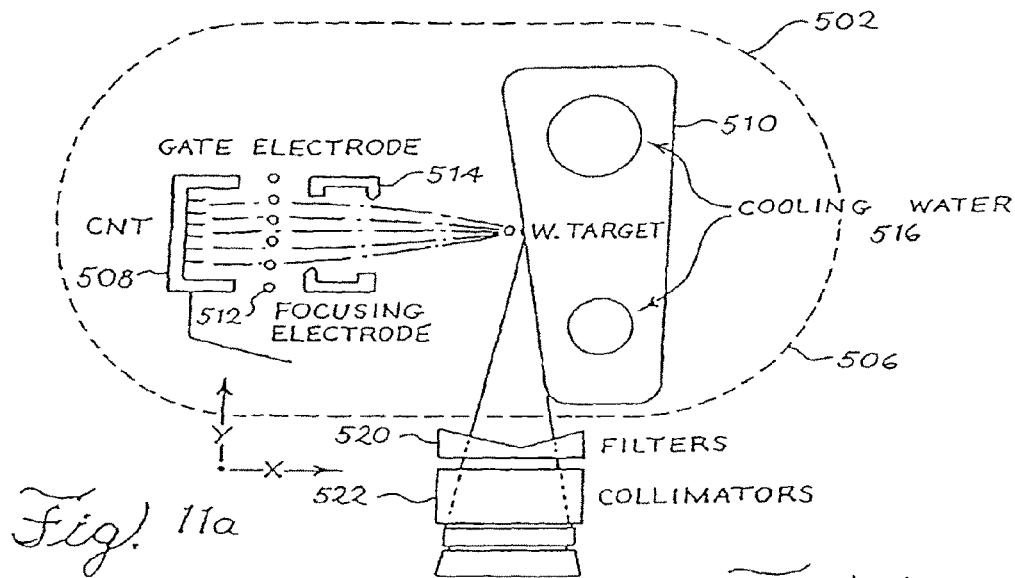
FIG. 11a schematically shows a side cross-sectional view of an embodiment of an x-ray source to be used with the quasi-cone-beam computed tomography system of FIG. 10 in accordance with the present invention.
Figure 11B:
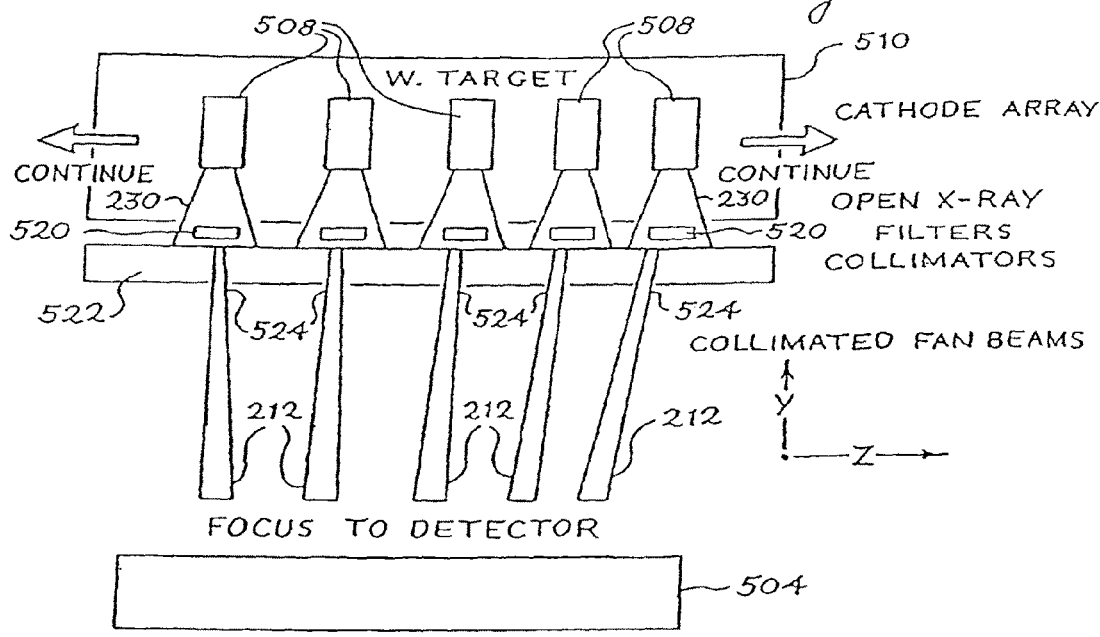

As shown in FIGS. 11*a-b*, the x-ray source 502 includes a single, cylindrical-like glass tube 506 within a vacuum pressure. The length of the tube 506 is approximately 38 cm along the z-direction and covers 19 cm in the z-direction at the isocenter. A plurality of carbon nanotube cathodes 508, such as 20 in total, are equally spaced from one another by approximately 2 cm. In the alternative, each cathode 508 can be replaced by a corresponding metallic filament that is heated to a temperature so that the electrons can be pulled out by establishing a potential between the cathode and the gate electrode 512.

Operation of a single nanotube cathode 508 is easily understood. In particular, a potential applied between cathode 508 and an anode 510 produces high local fields, as a result of the small radius of the nano fiber tip and the length of the nano fiber. These high local fields cause electrons to tunnel from the nanotube tip into the vacuum. An example of such a nanotube is commercially available from Xintek, Inc., wherein currents as high as 500 mA are available.

Electrons are pulled out from the carbon nanotube cathode 508 by the potential $V_g$ applied between the gate electrode 512 and the cathode 508. The electrons are accelerated by potential $V_a$, and focused into a small focus spot by potential $V_f$ and focusing electrodes 514. X-ray photons are generated via the bremsstrahlung effect when electrons strike on the molybdenum or tungsten anode target 510 and have an energy of about 80-130 keV when imaging a human. The focusing electrodes 514 direct the electrons to different portions of the anode target 510 to generate individual x-ray beams in a manner similar to that described with respect to the x-ray source 202 of FIGS. 9*a-b*. To prevent overheating of the anode 510, conduits 516 are formed within the anode 510 through which cooling water is circulated. The tube current, i.e., the current of the electrons striking the anode 510 is preferably about 167 mA.

As shown in FIGS. 11*a-b*, the x-ray source 502 includes a single anode 510 and a plurality of the cathodes 508 of FIG. 11*c*, wherein each cathode 508 is controlled by a controller, such as MOSFET controller not shown, to activate them in a desired sequence and at a desired current.

The cathodes 508 are activated sequentially as described below in order to generate a plurality of x-ray beams that strike discrete areas of space occupied by the anode 510. In operation, a variable DC voltage, $V_g$(<1 kV) is applied to the gate electrodes to extract the electrons from the cathodes 508. A separate controller or computer 234 can be used to control the controller circuit. Electrons are emitted from this activated cathode 508 when $V_g$ is larger than the critical field for emission. To generate a scanning x-ray beam from different origins on the target, a pulsed controlling signal with pre-determined pulse width is swept across the individual controller. At each point, the channel is "opened" to generate an electron beam from the particular cathode 508 which produces an x-ray beam from the corresponding focal point on the anode.

The cathodes 508 are sequentially switched on and off at a rate of approximately 300 Hz by programming the gate electrode 512, assuming a gantry rotation speed of 60 s/rev, and 600 projections, the tube's z-scanning period is about 0.1 second, 20 cathodes and 50% detector deadtime. Rates of greater than 100 kHz are also possible. As shown in FIG. 11*b*, the electrons emanating from each cathode 508 strike a different portion of the anode 510 and so a plurality of x-ray beams 230 are formed sequentially at different positions along the z-axis. The x-ray beams 230 pass through corresponding filters 520 and a stationary (relative to the x-ray source 502) collimator 522. The collimator 522 define slots 524 which correspond to the cathodes 508 in a one-to-one manner. The slots 524 can be rectangular in shape with a width less than that of the beams 230 so that fan beams 212 are formed and which are directed to detector 504, as shown in FIGS. 10 and 11*b*. With the sequential switching on and off of the cathodes 508 a fan shaped beam sweeps across the patient or object to be imaged. During this process, the drum 210 slowly rotates around the patient so that a plurality of two-dimensional images are captured that can be used to generate a three-dimensional quasi-cone-beam computed tomography image.

Figure 12:
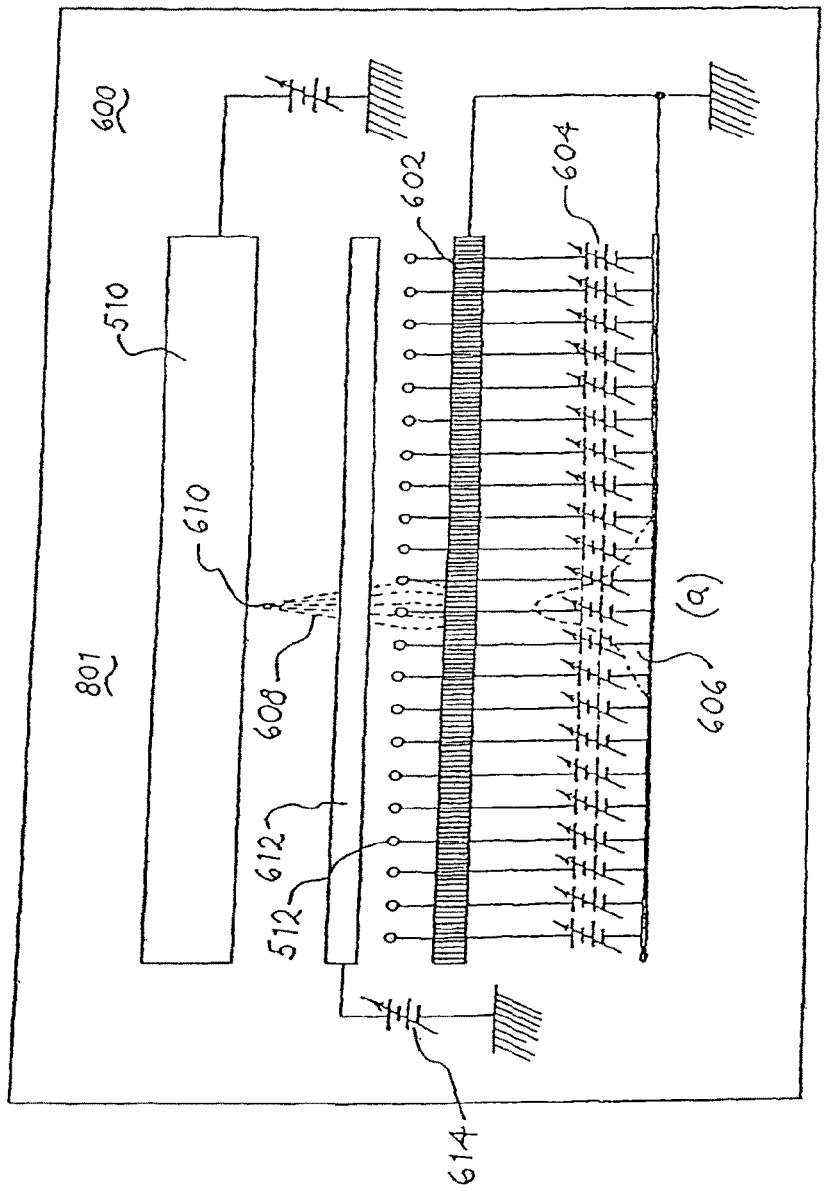
FIG. 12 schematically shows a side cross-sectional view of a second embodiment of an x-ray source to be used with the quasi-cone-beam computed tomography system of FIG. 10 in accordance with the present invention.

As an alternative, the x-ray source 502 of FIGS. 10-11 can be replaced with x-ray source 600, schematically shown in FIG. 12. In this embodiment, the cathode 602 is continuous line-shaped. Voltages 604 applied to a grid of gate electrodes 512 pull out electrons at different positions. This is controlled by applying gate voltages 604 at different gates. Each electrode's potential 604 can be controlled individually. A designed gate voltage profile 606 can be formed to focus the electrons 608 to a focus spot 610 in one dimension. The electrons 608 can be focused in the other dimension by gate 612 and its voltage 614. By programming the gate voltages, the x-ray beams can scan along the anode 510. The major advantage of this embodiment, as compared to the discrete cathode approach in FIGS. 12*a-c*, is that the x-ray beam scanning spatial resolution can be much higher. The focus spot 610 can be any position along the anode 510.

Figure 13A:
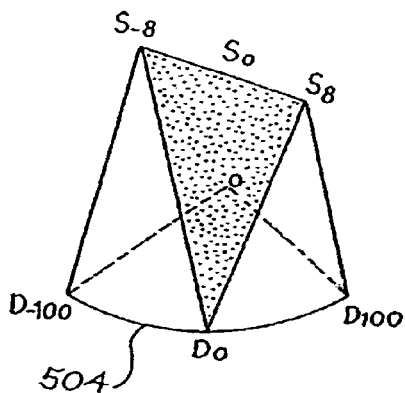
FIGS. 13a-c schematically shows an embodiment of a detector system to be used with the quasi-cone-beam computed tomography system of FIGS. 10-11 in accordance with the present invention FIGS. 14a-b schematically shows a second embodiment of a detector system to be used with the quasi-cone-beam computed tomography system of FIG. 11 in accordance with the present invention.

One possible variation for system 500 (whether using the x-ray source of FIG. 11 or FIG. 12) is to use rectangular slots 524 for the collimator 522 and to focus the individual detecting elements of detector 504 toward the rotation isocenter, O, as shown in FIGS. 10 and 13*a*. While this variation is not ideal, it does illustrate the relationship between quasi-cone-beam computed tomography and traditional cone-beam computed tomography. For example, FIG. 13*a* illustrates the scanning of an x-ray beam 212 across a patient or object at a single position of the x-ray source 502, 600 and detector array 504, wherein the x-ray source 502, 600 is perpendicular to the linear detector array 504. The term $S_n$ represents each individual focus spot where the electrons strike the anode 510. The term $D_n$, represents the position of each individual detector of the detector 504. As explained previously, the x-ray beam generated at a focus spot is collimated by a corresponding slot 524 into a fan-shaped beam 212. A fan-shape beam is indicated in FIG. 13*a* by the triangle area $S_n$-$D_{100}$-$D_{-100}$. As the x-ray beam scans along $S_8$-$S_{-8}$, it forms a tetrahedron volume. Thus, the volume scanned at a single position of the x-ray source 502, 600 and detector array 504 is not cone-shaped, which is formed by a point source and a two-dimensional detector in conventional cone-beam computed tomography. I refer the new imaging system as quasi cone-beam computed tomography to distinguish it from traditional cone-beam system. Note that as an alternative, the curved detector array can be replaced with a linear detector array.

Figure 13B:
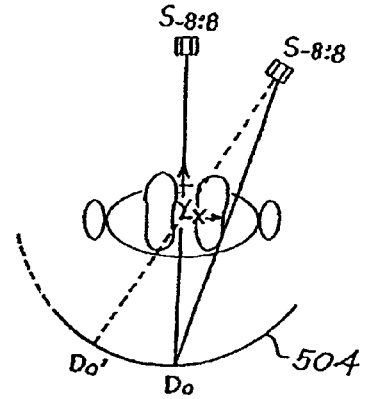

FIG. 13*b* shows the volumes scanned at multiple gantry positions by quasi-cone-beam computed tomography, wherein $D_{-100}$-$D_0$-$D_{100}$ are the discrete detectors of detector 504 and $S_{-8}$-$S_0$-$S_8$ are the x-ray beams 212 emanating from the slots 524 of collimator 522. As shown in FIG. 13*a*, $D_0$-$S_{-8}$-$S_8$ form a triangular plane. While the drum 210 (or support 308 of FIG. 2*b* or C-arm 218 of FIG. 2*c*) rotates clockwise, the detector $D_0$ moves to $D_0'$, and the x-ray beams move to $S_{-8:8}'$, as shown in FIG. 13*b*. Another detector occupies exactly the same position as the original position of $D_0$. A new plane with tilted angle is formed by this detector and source array $S_{-8}'$-

Figure 13C:
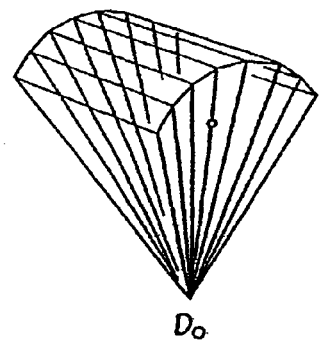

$S_8'$. As rotation continues, more and more planes are formed with larger cone angles. A cone volume is obtained by stacking these planes together, as shown in FIG. 13c. Thus, by resorting the data, the quasi-cone-beam computed tomography geometry is exactly the same as a conventional cone-beam computed tomography system. The same image reconstruction algorithms used for conventional cone-beam computed tomography can be used for image reconstruction for quasi-cone-beam computed tomography.

Figure 14A:
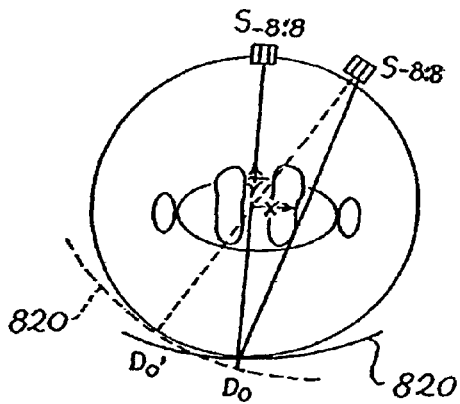
Figure 14B:
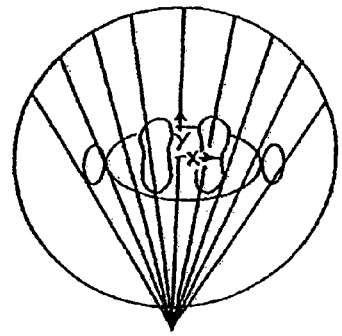

As mentioned previously, having the individual detecting elements of the detector 504 focused on the rotation isocenter is not an optimal design. An optimum variation of system 500 is to have the individual detector elements of detector 504 focused on the x-ray source 502 so that x-ray cross-talking is minimized and collimators can be used to further reject scatters. This configuration also provides easier mounting a collimator grid on the detectors to provide further rejection of in-plane scattering. In this variation, quasi-cone-beam computed tomography is slightly different from cone-beam computed tomography in geometry as shown in FIG. 14a. The configuration is the same as in FIG. 13b except that the detectors focus to the x-ray sources. The detector on the line $S_{-8:8}$-$D_0$ is not exactly located at the original position of the detector $D_0$ after the gantry rotates to another angle. It is shifted down slightly. The shifting increases with gantry angle. Thus, the cone, after re-sorting, does not have a unique vertex as shown schematically in FIG. 14b.

Note that for the embodiment of linear scanning x-ray source using discrete cathodes shown in FIGS. 11a-c, the x-ray beams scan with finite step size, such as 1 cm, due to the size of each individual cathode. In order to achieve higher image resolution in axial direction, the single-row detector array 504 is replaced by a multi-row linear detector array. The detector dimension can be much smaller than the spacing between the cathodes. Thus, the axial resolution can be increased. Isotropic resolution can be achieved if each individual detector is square-shaped.

The beam-eye view of the x-ray sources offside the central plane, such as $S_8$, the curved detector array is not straight as shown in FIG. 15a. To accommodate this, the collimator slot openings should be curved for offside x-ray sources as shown in FIG. 15b. The collimator 700 has a straight opening in the center and curved openings with gradually increased curvatures offside. The curvature of the slot opening is determined by the curvature of the detector in the beam eye view of the corresponding beam.

Now referring to FIG. 16, a flat panel detector 206 can be used in a quasi-cone-beam tomography system. The scanning x-ray beams 212 from sources 502 or 600 are still collimated to be fan-shaped. Each fan beam is perpendicular to the surface of flat panel detector 206. Each fan beam 212 directly irradiates a narrow slit area 236 of detector 206 if no patient P presented. Other areas of the detector 206 receive only scatter and so are not read out as described previously with respect to FIG. 4. Thus, the majority of scatter is rejected. The advantage of this embodiment is the simplicity of obtaining exactly reconstructed images. No complicated scanning loci are necessary. Robust and efficient Feldkamp-type reconstruction algorithms can be used and so there is no artifact from approximate cone beam reconstruction. A single axial scan does not satisfy data sufficient condition for exact cone beam computed tomography reconstruction. Approximate reconstruction causes some artifacts when the cone angle is large. The disadvantage is that the performance of flat panel detectors is currently not as good as discrete detectors.

An alternative embodiment of the system shown in FIG. 16 is to use focused multi-row detector to replace flat panel detector 206. This is the situation in multi-row helical CT scanner. In conventional helical CT scanner, when the number of rows of detectors increases, the cone angle becomes larger. Scatters and approximate reconstruction increase with cone angle. The advantage of this embodiment is that scatters can be largely rejected. Another advantage is the cone angle is small for each x-ray source.

Figure 1:
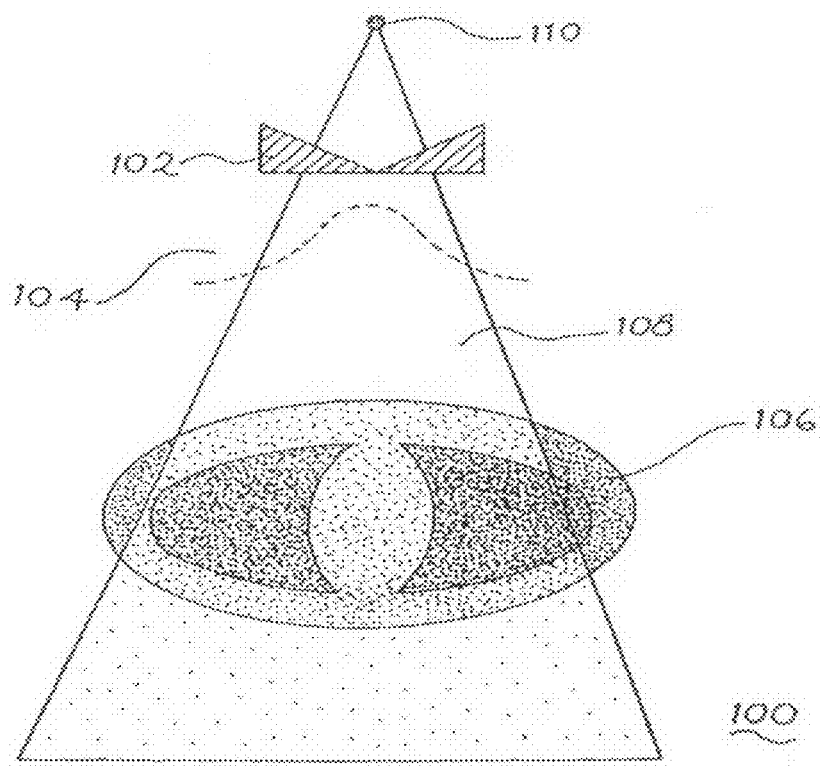
FIG. 1 depicts a known cone-beam computed tomography system using a bowtie filter.

Since the absorption through the patient is variable, modulation of the X-ray intensity optimizes the imaging process. For example, in the region of the patient where absorption is high, the X-ray intensity can be increased, and where the absorption is low, the intensity can be decreased. As such, the radiation dose to the patient can be reduced and the saturation of the detector can be avoided. As described previously with respect to FIG. 1, bow-tie filter 102 has been used in the past to modulate the beam intensity profile across the patient. The present invention avoids the use of a bow-tie filter by modulating the intensity of the fan beams of the systems of FIGS. 2-16 by dynamically controlling the tube current (mA) of each individual fan beam 212 via a controller or via a controller in computer 234. Dynamic mA control can also be combined with a bow-tie filter so that the beam intensity can be modulated two dimensionally.

The advantage of modulating beam profile with dynamic mA control of each individual fan beam is that the profile can be adjusted easily by programming the tube current. The profile can be changed dynamically based of the thickness of body that the beam will pass through. Thickness depends on the shape of the imaged object as well as the gantry angle.

Now referring to FIGS. 3, 9 and 11, the thickness of the patient P can be calculated for each individual fan beam 212 (FIG. 3), 230 (FIG. 9), 212 (FIG. 11). The optimal tube current mA can be calculated and programmed based on the calculated thickness. During the scan, the beam intensity is controlled in preprogrammed pattern.

In another embodiment the dynamic mA control includes adjusting the tube current in real-time. The signal intensity of one fan beam can be processed. The optimal intensity of a second fan beam that immediately follows the one fan beam can be determined by assuming the patient geometry is similar to that of the one fan beam. The second fan beam is delivered with a calculated optimal intensity. The signal of the second fan beam can be used to determine the intensities of the beams after that. This process is repeated for subsequent fan beams until scanning is finished. The delivered intensities of each fan beam need to be recorded for reconstruction.

The embodiments of the invention described above can be implemented in various cone (wide) beam computed tomography systems, including on-board cone-beam computed tomography radiotherapy units, multi-row detector helical computed tomography systems, multi-row detector axial computed tomography systems, and C-arm flat panel cone-beam computed tomography systems, as well as other conventional diagnostic computed tomography systems. The applications of quasi-cone-beam computed tomography can be employed in other forms of image guided interventions, such as image-guided surgery/biopsy with C-arm cone-beam computed tomography. The scatter rejection mechanism of quasi-cone-beam computed tomography is also applicable to multi-row (as many as 1024 now) helical scanners and digital tomosynthesis.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

I claim:

1. A cone-beam computed tomography system comprising:
   an x-ray source that emits an x-ray beam;
   a slot that intercepts said x-ray beam so that a plurality of fan-shaped x-ray beams emanate from said slot towards an object;
   a detector receiving fan-shaped x-rays after said fan-shaped x-ray beams pass through said object, said detector generating an imaging signal for each of said received fan-shaped x-rays; and
   a computer connected to said detector so as to receive said imaging signals for each of said received fan-shaped x-rays, wherein said x-ray source, said slot and said detector move relative to said object so that multiple imaging signals are reconstructed by said computer to generate a three-dimensional cone-beam computed tomography image therefrom; and
   a display connected to said computer and displaying said three-dimensional cone-beam computed tomography image; and
   wherein said slot moves relative to said x-ray source.

2. The cone-beam computed tomography system of claim 1, wherein said x-ray source comprises a kV x-ray source.

3. The cone-beam computed tomography system of claim 1, wherein said slot rotates about said x-ray source.

4. The cone-beam computed tomography system of claim 1, wherein said slot is stationary with respect to a housing that contains said x-ray source.

5. The cone-beam computed tomography system of claim 4, wherein said x-ray source comprises an anode and a cathode, wherein said cathode emits electrons which strike multiple, discrete areas of space occupied by said anode.

6. The cone-beam computed tomography system of claim 1, wherein said detector is a flat panel imager.

7. The cone-beam computed tomography system of claim 6, wherein said flat panel imager comprises an array of amorphous silicon detector elements.

8. The cone-beam computed tomography system of claim 7, wherein said array is a two-dimensional array.

9. The cone-beam computed tomography system of claim 1, wherein said x-ray source comprises an anode and a cathode, wherein said cathode emits electrons which strike a single area of space occupied by said anode.

10. The cone-beam computed tomography system of claim 1, wherein said x-ray source comprises an anode and a cathode, wherein said cathode emits electrons which strike multiple, discrete areas of space occupied by said anode.

11. The cone-beam computed tomography system of claim 1, wherein said computer causes said detector to read only certain areas of said detector for each fan-shaped x-ray beam received.

12. The cone-beam computed tomography system of claim 1, wherein said x-ray source comprises a source of particles that strike a target, wherein an intensity of each of said plurality of fan-shaped x-ray beams is modulated by modulating a current of said particles striking said target.

13. A method of imaging an object, comprising:
   i) emitting from an x-ray source an x-ray beam in a fan-shaped form towards an object;
   ii) detecting x-rays that pass through said object due to said emitting an x-ray beam with a detector;
   iii) generating image data regarding said object from said detected x-rays; and
   iv) rotating said x-ray source and said detector relative to said object and continuously repeating steps i)-iv) until a sufficient number of imaging data regarding said object is generated so as to form a three-dimensional cone-beam computed tomography image therefrom;
   forming a three-dimensional cone-beam computed tomography image from said sufficient number of imaging data; and
   displaying said three-dimensional cone-beam computed tomography image; and
   wherein said emitting comprises collimating a single x-ray beam with a collimator moving relative to said x-ray source.

14. The method of claim 13, wherein said three-dimensional cone-beam computed tomography image is formed from at most one full rotation of said x-ray source and detector about said object.

15. The method of claim 13, wherein said moving collimator rotates.

16. The method of claim 13, wherein said emitting comprises sequentially forming x-ray beams off of different areas of an anode of said x-ray source.

17. The method of claim 16, wherein said emitting comprises sequentially forming x-ray beams off of said different areas of said anode by sequentially directing electrons from a single cathode of said x-ray source towards said different areas.

18. The method of claim 13, wherein said x-ray beam has an energy in a kilovolt range.

19. The method of claim 13, further comprising modulating intensities of each of said plurality of fan-shaped x-ray beams by modulating a current of particles striking a target that generate said plurality of fan-shaped x-ray beams.

* * * * *